US006716627B2

United States Patent
Dobie

(12) United States Patent
(10) Patent No.: US 6,716,627 B2
(45) Date of Patent: Apr. 6, 2004

(54) ANTISENSE MODULATION OF MUCIN 1, TRANSMEMBRANE EXPRESSION

(75) Inventor: Kenneth W. Dobie, Del Mar, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 140 days.

(21) Appl. No.: 10/029,517

(22) Filed: Dec. 20, 2001

(65) Prior Publication Data

US 2003/0148969 A1 Aug. 7, 2003

(51) Int. Cl.⁷ .......................... C07H 21/04; C12Q 1/68; C12N 15/85; C12N 15/86; C12P 19/34
(52) U.S. Cl. ..................... 435/375; 435/325; 435/91.1; 435/91.3; 536/23.1; 536/23.2; 536/24.5; 536/24.3; 536/24.31; 536/24.33
(58) Field of Search .................... 435/6, 91.1, 91.3, 435/325, 375; 536/23.1, 23.2, 24.5, 24.3, 24.31, 24.33; 514/44

(56) References Cited

U.S. PATENT DOCUMENTS

| 5,801,154 A | * | 9/1998 | Baracchini et al. ........... 514/44 |
| 5,861,381 A | | 1/1999 | Chambon et al. |
| 6,203,795 B1 | | 3/2001 | Chambon et al. |

FOREIGN PATENT DOCUMENTS

| EP | 1103623 | | 5/2001 |
| WO | WO 00/34468 | * | 12/1999 |

OTHER PUBLICATIONS

DW Green et al., American College of Surgeons, "Antisense Oligonucleotides:An Evolving Technology for the Modulation of Gene Expression in Human Disease," Jul. 2000, vol. 191, No.1, pp. 93–105.*
K–Y Jen et al., Stem Cells, "Suppression of Gene Expression by Targeted Disruption of Messenger RNA Available Options and Current Strategies," 2000, 18:307–319.*
S Agrawal et al., Molecular Medicine Today, "Antisense therapeutics:is it as simple as complementary base recognition?" Feb. 2000, vol. 6, pp. 72–81.*
AD Branch, TIBS, "A good antisense molecule is hard to find," Feb. 1998, pp. 45–50.*
Batenjany et al., The effect of cholesterol in a liposomal Muc1 vaccine, Biochim. Biophys. Acta, 2001, 1514:280–290.
Batra et al., Transfection of the human Muc 1 mucin gene into a poorly differentiated human pancreatic tumor cell line, Panc1: integration, expression and ultrastructural changes, J. Cell Sci., 1991, 100:841–849.
Batra et al., Expression of the human MUC1 mucin cDNA in a hamster pancreatic tumor cell line HP–1, Int. J. Pancreatol., 1992, 12:271–283.
Bergeron et al., MAUB is a new mucin antigen associated with bladder cancer, J. Biol. Chem., 1996, 271:6933–6940.

Burton et al., Epithelial mucin–1 (MUC1) expression and MA5 anti–MUC1 monoclonal antibody targeting in multiple myeloma, Clin. Cancer Res., 1999, 5:3065s–3072s.
Gendler et al., Molecular cloning and expression of human tumor–associated polymorphic epithelial mucin, J. Biol. Chem., 1990, 265:15286–15293.
Griffiths et al., Expression of the hypervariable PUM locus in normal and malignant lung: the tumor–associated epitopes are present but masked in normal tissue, Dis. Markers, 1988, 6:195–202.
Hough et al., Large–scale serial analysis of gene expression reveals genes differentially expressed in ovarian cancer, Cancer Res., 2000, 60:6281–6287.
Irimura et al., Diverse glycosylation of MUC1 and MUC2: potential signifigance in tumor immunity, J. Biochem. (Tokyo), 1999, 126:975–985.
Kardon et al., Bacterial conjunctivitis in Muc1 null mice, Invest. Ophthalmol. Vis. Sci., 1999, 40:1328–1335.
Karlsson et al., A genetic polymorphism of a human urinary mucin, Ann. Hum. Genet., 1983, 47:263–269.
Kondo et al., Decreased MUC1 expression induces E–cadherin–mediated cell adhesion of breast cancer cell lines, Cancer Res., 1998, 58:2014–2019.
Lan et al., Cloning and sequencing of a human pancreatic tumor mucin cDNA, J. Biol. Chem., 1990, 265:15294–15299.
Mather et al., The distribution of MUC1, an apical membrane glycoprotein, in mammary epithelial cells at the resolution of the electron microscope: implications for the mechanism of milk secretion, Cell Tissue Res., 2001, 304:91–101.
Middleton–Price et al., Close linkage of PUM and SPTA within chromosome band 1q21, Ann. Hum. Genet., 1988, 52:273–278.
Mukherjee et al., Mice with spontaneous pancreatic cancer naturally develop MUC–1–specific CTLs that eradicate tumors when adoptively transferred, J. Immunol., 2000, 165:3451–3460.
Obermair et al., Novel muc1 splice variants are expressed in cervical carcinoma, Gynecol. Oncol., 2001, 83:343–347.
Patton et al., The epithelial mucin, MUC1, of milk, mammary gland and other tissues, Biochim. Biophys. Acta, 1995, 1241:407–423.
Rahn et al., The importance of MUC1 cellular localization in patients with breast carcinoma: an immunohistologic study of 71 patients and review of the literature, Cancer, 2001, 91:1973–1982.

(List continued on next page.)

Primary Examiner—Karen Lacourciere
(74) Attorney, Agent, or Firm—Licata & Tyrrell P.C.

(57) ABSTRACT

Antisense compounds, compositions and methods are provided for modulating the expression of mucin 1, transmembrane. The compositions comprise antisense compounds, particularly antisense oligonucleotides, targeted to nucleic acids encoding mucin 1, transmembrane. Methods of using these compounds for modulation of mucin 1, transmembrane expression and for treatment of diseases associated with expression of mucin 1, transmembrane are provided.

13 Claims, No Drawings

OTHER PUBLICATIONS

Swallow et al., The human tumour–associated epithelial mucins are coded by an expressed hypervariable gene locus PUM, *Nature*, 1987, 328:82–84.

Swallow et al., The hypervariable gene locus PUM, which codes for the tumour associated epithelial mucins, is located on chromosome 1, within the region 1q21–24, *Ann. Hum.Genet.*, 1987, 51:289–294.

Swallow et al., Linkage between the expressed hypervariable gene locus PUM and the gene coding for the Duffy blood group FY, *Ann. Hum. Genet.*, 1988, 52:269–271.

Vaughn et al., The immune response of mice and cynomolgus monkeys to macaque mucin 1–mannan, *Vaccine*, 2000, 18:3297–3309.

Yu et al., Mucin mRNA expression in lung adenocarcinoma cell lines and tissues, *Oncology*, 1996, 53:118–126.

* cited by examiner

SEQUENCE LISTING

<160> NUMBER OF SEQ ID NOS: 107

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                           20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                           20

<210> SEQ ID NO 3
<211> LENGTH: 1721
<212> TYPE: DNA
<213> ORGANISM: Homo sapiens
<220> FEATURE:
<221> NAME/KEY: CDS
<222> LOCATION: (58)...(1605)

<400> SEQUENCE: 3
gaattccctg gctgcttgaa tctgttctgc cccctcccca cccatttcac caccacc      57 atg aca ccg ggc acc cag tct cct ttc ttc ctg ctg ctg ctc ctc aca   105
Met Thr Pro Gly Thr Gln Ser Pro Phe Phe Leu Leu Leu Leu Leu Thr
 1               5                  10                  15 gtg ctt aca gtt gtt aca ggt tct ggt cat gca agc tct acc cca ggt   153
Val Leu Thr Val Val Thr Gly Ser Gly His Ala Ser Ser Thr Pro Gly
            20                  25                  30 gga gaa aag gag act tcg gct acc cag aga agt tca gtg ccc agc tct   201
Gly Glu Lys Glu Thr Ser Ala Thr Gln Arg Ser Ser Val Pro Ser Ser
        35                  40                  45 act gag aag aat gct gtg agt atg acc agc agc gta ctc tcc agc cac   249
Thr Glu Lys Asn Ala Val Ser Met Thr Ser Ser Val Leu Ser Ser His
     50                  55                  60 agc ccc ggt tca ggc tcc tcc acc act cag gga cag gat gtc act ctg   297
Ser Pro Gly Ser Gly Ser Ser Thr Thr Gln Gly Gln Asp Val Thr Leu
 65                  70                  75                  80 gcc ccg gcc acg gaa cca gct tca ggt tca gct gcc acc tgg gga cag   345
Ala Pro Ala Thr Glu Pro Ala Ser Gly Ser Ala Ala Thr Trp Gly Gln
                85                  90                  95 gat gtc acc tcg gtc cca gtc acc agg cca gcc ctg ggc tcc acc acc   393
Asp Val Thr Ser Val Pro Val Thr Arg Pro Ala Leu Gly Ser Thr Thr
                100                 105                 110 ccg cca gcc cac gat gtc acc tca gcc ccg gac aac aag cca gcc ccg   441
Pro Pro Ala His Asp Val Thr Ser Ala Pro Asp Asn Lys Pro Ala Pro
            115                 120                 125 ggc tcc acc gcc ccc cca gcc cac ggt gtc acc tcg gcc ccg gac acc   489
Gly Ser Thr Ala Pro Pro Ala His Gly Val Thr Ser Ala Pro Asp Thr
        130                 135                 140 agg ccg ccc ccg ggc tcc acc gcc ccc cca gcc cac ggt gtc acc tcg   537
Arg Pro Pro Pro Gly Ser Thr Ala Pro Pro Ala His Gly Val Thr Ser
145                 150                 155                 160

```
gcc ccg gac acc agg ccg ccc ccg ggc tcc acc gcg ccc gca gcc cac      585
Ala Pro Asp Thr Arg Pro Pro Pro Gly Ser Thr Ala Pro Ala Ala His
            165                 170                 175 ggt gtc acc tcg gcc ccg gac acc agg ccg gcc ccg ggc tcc acc gcc      633
Gly Val Thr Ser Ala Pro Asp Thr Arg Pro Ala Pro Gly Ser Thr Ala
        180                 185                 190 ccc cca gcc cat ggt gtc acc tcg gcc ccg gac aac agg ccc gcc ttg      681
Pro Pro Ala His Gly Val Thr Ser Ala Pro Asp Asn Arg Pro Ala Leu
            195                 200                 205 gcg tcc acc gcc cct cca gtc cac aat gtc acc tcg gcc tca ggc tct      729
Ala Ser Thr Ala Pro Pro Val His Asn Val Thr Ser Ala Ser Gly Ser
        210                 215                 220 gca tca ggc tca gct tct act ctg gtg cac aac ggc acc tct gcc agg      777
Ala Ser Gly Ser Ala Ser Thr Leu Val His Asn Gly Thr Ser Ala Arg
225                 230                 235                 240 gct acc aca acc cca gcc agc aag agc act cca ttc tca att ccc agc      825
Ala Thr Thr Thr Pro Ala Ser Lys Ser Thr Pro Phe Ser Ile Pro Ser
            245                 250                 255 cac cac tct gat act cct acc acc ctt gcc agc cat agc acc aag act      873
His His Ser Asp Thr Pro Thr Thr Leu Ala Ser His Ser Thr Lys Thr
        260                 265                 270 gat gcc agt agc act cac cat agc acg gta cct cct ctc acc tcc tcc      921
Asp Ala Ser Ser Thr His His Ser Thr Val Pro Pro Leu Thr Ser Ser
            275                 280                 285 aat cac agc act tct ccc cag ttg tct act ggg gtc tct ttc ttt ttc      969
Asn His Ser Thr Ser Pro Gln Leu Ser Thr Gly Val Ser Phe Phe Phe
        290                 295                 300 ctg tct ttt cac att tca aac ctc cag ttt aat tcc tct ctg gaa gat     1017
Leu Ser Phe His Ile Ser Asn Leu Gln Phe Asn Ser Ser Leu Glu Asp
305                 310                 315                 320 ccc agc acc gac tac tac caa gag ctg cag aga gac att tct gaa atg     1065
Pro Ser Thr Asp Tyr Tyr Gln Glu Leu Gln Arg Asp Ile Ser Glu Met
            325                 330                 335 ttt ttg cag att tat aaa caa ggg ggt ttt ctg ggc ctc tcc aat att     1113
Phe Leu Gln Ile Tyr Lys Gln Gly Gly Phe Leu Gly Leu Ser Asn Ile
        340                 345                 350 aag ttc agg cca gga tct gtg gtg gta caa ttg act ctg gcc ttc cga     1161
Lys Phe Arg Pro Gly Ser Val Val Val Gln Leu Thr Leu Ala Phe Arg
            355                 360                 365 gaa ggt acc atc aat gtc cac gac gtg gag aca cag ttc aat cag tat     1209
Glu Gly Thr Ile Asn Val His Asp Val Glu Thr Gln Phe Asn Gln Tyr
        370                 375                 380 aaa acg gaa gca gcc tct cga tat aac ctg acg atc tca gac gtc agc     1257
Lys Thr Glu Ala Ala Ser Arg Tyr Asn Leu Thr Ile Ser Asp Val Ser
385                 390                 395                 400 gtg agt gat gtg cca ttt cct ttc tct gcc cag tct ggg gct ggg gtg     1305
Val Ser Asp Val Pro Phe Pro Phe Ser Ala Gln Ser Gly Ala Gly Val
            405                 410                 415 cca ggc tgg ggc atc gcg ctg ctg gtg ctg gtc tgt gtt ctg gtt gcg     1353
Pro Gly Trp Gly Ile Ala Leu Leu Val Leu Val Cys Val Leu Val Ala
        420                 425                 430 ctg gcc att gtc tat ctc att gcc ttg gct gtc tgt cag tgc cgc cga     1401
Leu Ala Ile Val Tyr Leu Ile Ala Leu Ala Val Cys Gln Cys Arg Arg
            435                 440                 445 aag aac tac ggg cag ctg gac atc ttt cca gcc cgg gat acc tac cat     1449
Lys Asn Tyr Gly Gln Leu Asp Ile Phe Pro Ala Arg Asp Thr Tyr His
        450                 455                 460 cct atg agc gag tac ccc acc tac cac acc cat ggg cgc tat gtg ccc     1497
Pro Met Ser Glu Tyr Pro Thr Tyr His Thr His Gly Arg Tyr Val Pro
465                 470                 475                 480
```

```
cct agc agt acc gat cgt agc ccc tat gag aag gtt tct gca ggt aat    1545
Pro Ser Ser Thr Asp Arg Ser Pro Tyr Glu Lys Val Ser Ala Gly Asn
            485                 490                 495 ggt ggc agc agc ctc tct tac aca aac cca gca gtg gca gcc act tct    1593
Gly Gly Ser Ser Leu Ser Tyr Thr Asn Pro Ala Val Ala Ala Thr Ser
        500                 505                 510 gcc aac ttg tag gggcacgtcg ccctctgagc tgagtggcca gccagtgcca        1645
Ala Asn Leu
        515 ttccactcca ctcagggctc tctgggccag tcctcctggg agcccccacc acaacacttc  1705 ccaggcatgg aattcc                                                  1721

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
tgactctggc cttccgagaa                                                 20

<210> SEQ ID NO 5
<211> LENGTH: 24
<212> TYPE: DNA
<213> ORGANISM: Artificial Sequence
<220> FEATURE:
<223> OTHER INFORMATION: PCR Primer

<400> SEQUENCE: 5
gctgcttccg ttttatactg attg                                            24

<210> SEQ ID NO 6
<211> LENGTH: 28
<212> TYPE: DNA
<213> ORGANISM: Artificial Sequence
<220> FEATURE:
<223> OTHER INFORMATION: PCR Probe

<400> SEQUENCE: 6
taccatcaat gtccacgacg tggagaca                                        28

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                  19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                 20

<210> SEQ ID NO 9
<211> LENGTH: 20
```

-continued

```
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                              20

<210> SEQ ID NO 10
<211> LENGTH: 759
<212> TYPE: DNA
<213> ORGANISM: Homo sapiens
<220> FEATURE:
<221> NAME/KEY: CDS
<222> LOCATION: (1)...(759)

<400> SEQUENCE: 10 atg aca ccg ggc acc cag tct cct ttc ttc ctg ctg ctg ctc ctc aca     48
Met Thr Pro Gly Thr Gln Ser Pro Phe Phe Leu Leu Leu Leu Leu Thr
 1               5                  10                  15 gtg ctt aca ggt tct ggt cat gca agc tct acc cca ggt gga gaa aag     96
Val Leu Thr Gly Ser Gly His Ala Ser Ser Thr Pro Gly Gly Glu Lys
             20                  25                  30 gag act tcg gct acc cag aga agt tca gtg ccc agc tct act gag aag    144
Glu Thr Ser Ala Thr Gln Arg Ser Ser Val Pro Ser Ser Thr Glu Lys
         35                  40                  45 aat gct ttt aat tcc tct ctg gaa gat ccc agc acc gac tac tac caa    192
Asn Ala Phe Asn Ser Ser Leu Glu Asp Pro Ser Thr Asp Tyr Tyr Gln
     50                  55                  60 gag ctg cag aga gac att tct gaa atg ttt ttg cag att tat aaa caa    240
Glu Leu Gln Arg Asp Ile Ser Glu Met Phe Leu Gln Ile Tyr Lys Gln
 65                  70                  75                  80 ggg ggt ttt ctg ggc ctc tcc aat att aag ttc agg cca gga tct gtg    288
Gly Gly Phe Leu Gly Leu Ser Asn Ile Lys Phe Arg Pro Gly Ser Val
                 85                  90                  95 gtg gta caa ttg act ctg gcc ttc cga gaa ggt acc atc aat gtc cac    336
Val Val Gln Leu Thr Leu Ala Phe Arg Glu Gly Thr Ile Asn Val His
            100                 105                 110 gac atg gag aca cag ttc aat cag tat aaa acg gaa gca gcc tct cga    384
Asp Met Glu Thr Gln Phe Asn Gln Tyr Lys Thr Glu Ala Ala Ser Arg
        115                 120                 125 tat aac ctg acg atc tca gac gtc agc gtg agt gat gtg cca ttt cct    432
Tyr Asn Leu Thr Ile Ser Asp Val Ser Val Ser Asp Val Pro Phe Pro
    130                 135                 140 ttc tct gcc cag tct ggg gct ggg gtg cca ggc tgg ggc atc gcg ctg    480
Phe Ser Ala Gln Ser Gly Ala Gly Val Pro Gly Trp Gly Ile Ala Leu
145                 150                 155                 160 ctg gtg ctg gtc tgt gtt ctg gtt gcg ctg gcc att gtc tat ctc att    528
Leu Val Leu Val Cys Val Leu Val Ala Leu Ala Ile Val Tyr Leu Ile
                165                 170                 175 gcc ttg gct gtc tgt cag tgc cgc cga aag aac tac ggg cag ctg gac    576
Ala Leu Ala Val Cys Gln Cys Arg Arg Lys Asn Tyr Gly Gln Leu Asp
            180                 185                 190 atc ttt cca gcc cgg gat acc tac cat cct atg agc gag tac ccc acc    624
Ile Phe Pro Ala Arg Asp Thr Tyr His Pro Met Ser Glu Tyr Pro Thr
        195                 200                 205 tac cac acc cat ggg cgc tat gtg ccc cct agc agt acc gat cgt agc    672
Tyr His Thr His Gly Arg Tyr Val Pro Pro Ser Ser Thr Asp Arg Ser
    210                 215                 220 ccc tat gag aag gtt tct gca ggt aat ggt ggc agc agc ctc tct tac    720
Pro Tyr Glu Lys Val Ser Ala Gly Asn Gly Gly Ser Ser Leu Ser Tyr
225                 230                 235                 240
```

```
aca aac cca gca gtg gca gcc act tct gcc aac ttg tag              759
Thr Asn Pro Ala Val Ala Ala Thr Ser Ala Asn Leu
            245                 250
```

<210> SEQ ID NO 11
<211> LENGTH: 543
<212> TYPE: DNA
<213> ORGANISM: Homo sapiens
<220> FEATURE:
<221> NAME/KEY: CDS
<222> LOCATION: (25)...(531)

<400> SEQUENCE: 11

```
ctccccaccc atttcaccac cacc atg aca ccg ggc acc cag tct cct ttc    51
                          Met Thr Pro Gly Thr Gln Ser Pro Phe
                           1               5 ttc ctg ctg ctg ctc aca gtg ctt aca gtt gtt aca ggt tct ggt       99
Phe Leu Leu Leu Leu Thr Val Leu Thr Val Val Thr Gly Ser Gly
 10              15                  20                  25 cat gca agc tct acc cca ggt gga gaa aag gag act tcg gct acc cag   147
His Ala Ser Ser Thr Pro Gly Gly Glu Lys Glu Thr Ser Ala Thr Gln
                30                  35                  40 aga agt tca gtg ccc agc tct act gag aag aat gct ttg tct act ggg   195
Arg Ser Ser Val Pro Ser Ser Thr Glu Lys Asn Ala Leu Ser Thr Gly
            45                  50                  55 gtc tct ttc ttt ttc ctg tct ttt cac att tca aac ctc cag ttt aat   243
Val Ser Phe Phe Phe Leu Ser Phe His Ile Ser Asn Leu Gln Phe Asn
        60                  65                  70 tcc tct ctg gaa gat ccc agc acc gac tac tac caa gag ctg cag aga   291
Ser Ser Leu Glu Asp Pro Ser Thr Asp Tyr Tyr Gln Glu Leu Gln Arg
 75                  80                  85 gac att tct gaa atg gct gtc tgt cag tgc cgc cga aag aac tac ggg   339
Asp Ile Ser Glu Met Ala Val Cys Gln Cys Arg Arg Lys Asn Tyr Gly
 90                  95                 100                 105 ctg ctg gac atc ttt cca gcc cgg gat acc tac cat cct atg agc gag   387
Leu Leu Asp Ile Phe Pro Ala Arg Asp Thr Tyr His Pro Met Ser Glu
                110                 115                 120 tac ccc acc tac cac acc cat ggg cgc tat gtg ccc cct agc agt acc   435
Tyr Pro Thr Tyr His Thr His Gly Arg Tyr Val Pro Pro Ser Ser Thr
            125                 130                 135 gat cgt agc ccc tat gag aag gtt tct gca ggt aat ggt ggc agc agc   483
Asp Arg Ser Pro Tyr Glu Lys Val Ser Ala Gly Asn Gly Gly Ser Ser
        140                 145                 150 ctc tct tac aca aac cca gca gtg gca gcc act tct gcc aac ttg tag   531
Leu Ser Tyr Thr Asn Pro Ala Val Ala Ala Thr Ser Ala Asn Leu
    155                 160                 165 gggcacgtcg cc                                                     543
```

<210> SEQ ID NO 12
<211> LENGTH: 122
<212> TYPE: DNA
<213> ORGANISM: Homo sapiens
<220> FEATURE:
<221> NAME/KEY: exon:exon junction
<222> LOCATION: (58)...(59)
<223> OTHER INFORMATION: exon 4:exon 6

<400> SEQUENCE: 12

```
atgttttttgc agatttataa acaagggggt tttctgggcc tctccaatat taagttcagt   60
```

```
gagtgatgtg ccatttcctt tctctgccca gtctggggct ggggtgccag gctggggcat    120
cg                                                                  122
```

<210> SEQ ID NO 13
<220> FEATURE:
<211> LENGTH:
<212> TYPE:
<213> ORGANISM:

<400> SEQUENCE: 13

000

<210> SEQ ID NO 14
<211> LENGTH: 577
<212> TYPE: DNA
<213> ORGANISM: Homo sapiens
<220> FEATURE:
<221> NAME/KEY: exon:exon junction
<222> LOCATION: (169)...(170)
<223> OTHER INFORMATION: exon 3c:exon 6b

<400> SEQUENCE: 14

```
cgtgtcgcga ctgctcacct cctccaatca cagcacttct ccccagttgt ctactggggt    60
ctctttcttt ttcctgtctt ttcacatttc aaacctccag tttaattcct ctctggaaga   120
tcccagcacc gactactacc aagagctgca gagagacatt tctgaaatgt ctggggctgg   180
ggtgccaggc tggggcatcg cgctgctggt gctggtctgt gttctggttg cgctggccat   240
tgtctatctc attgccttgg ctgtctgtca gtgccgccga aagaactacg ggcagctgga   300
catctttcca gcccgggata cctaccatcc tatgagcgag taccccacct accacaccca   360
tgggcgctat gtgcccccta gcagtaccga tcgtagcccc tatgagaagg ttttctgcagg   420 taatggtggc agcagcctct cttacacaaa cccagcagtg gcagccactt cttgcaactt   480 gtagggcac gtcgcccgct gagctgagta gccagccagt gccattccac tccactcagg   540
ttcttcaggg ccagagcccc tgcaccctgt ttgggct                            577
```

<210> SEQ ID NO 15
<220> FEATURE:
<211> LENGTH:
<212> TYPE:
<213> ORGANISM:

<400> SEQUENCE: 15

000

<210> SEQ ID NO 16
<211> LENGTH: 981
<212> TYPE: DNA
<213> ORGANISM: Homo sapiens
<220> FEATURE:
<221> NAME/KEY: exon:exon junction
<222> LOCATION: (464)...(465)
<223> OTHER INFORMATION: exon 3b:exon 4

<400> SEQUENCE: 16

```
gggacaccag gccggccccg ggctccaccg ccccccccagc ccatggtgtc acctcggccc    60
cggacaacag gccgccttg ggctccaccg cccctccagt ccacaatgtc acctcggcct    120
caggctctgc atcaggctca gcttctactc tggtgcacaa cagcacctct gccagggcta   180
ccacaacccc agccagcaag agcactccat tctcaattcc cagccaccac tctgatactc   240
```

-continued

```
ctaccaccct tgccagccat agcaccaaga ctgatgccag tagcactcac catagcacgg      300
tacctcctct cacctcctcc aatcacagca cttctcccca gttgtctact ggggtctctt      360 tcttttcct gtcttttcac atttcaaacc tccagtttaa ttcctctctg gaagatccca       420
gcaccgacta ctaccaagag ctgcagagag acatttctga atgtgagtg atgtgccatt       480 tcctttctct gcccagtctg gggctggggt gccaggctgg gcatcgcgc tgctggtgct       540 ggtctgtgtt ctggttgcgc tggccattgt ctatctcatt gccttggctg tctgtcagtg     600
ccgccgaaag aactacgggc agctggacat ctttccagcc cgggatacct accatcctat      660
gagcgagtac cccacctacc aacccatggg cgctatgtgc ccctagcag taccgatcgt      720 agcccctatg agacaggttt ctgcaggtaa tggtggcagc agctctctta cacaaaccag      780
cagtggcagc cacttctgcc aacttgtagg ggcacgttgc cgctgacctg agtggccagc      840
cagtgccatt ccacttccac tcagggttct tcaggggcca gagccctgca ccctgtttgg      900
cctggtgagc tggacttcaa ggtgggctgt cacagcctct tcaaaggccc acaattcttc      960
gacatcctca ggtgtggaag c                                               981
```

<210> SEQ ID NO 17
<211> LENGTH: 1804
<212> TYPE: DNA
<213> ORGANISM: Homo sapiens
<220> FEATURE:
<221> NAME/KEY: CDS
<222> LOCATION: (73)...(1500)

<400> SEQUENCE: 17

```
cgctccacct ctcaagcagc cagcgcctgc ctgaatctgt tctgccccct ccccacccat       60
ttcaccacca cc atg aca ccg ggc acc cag tct cct ttc ttc ctg ctg ctg    111
              Met Thr Pro Gly Thr Gln Ser Pro Phe Phe Leu Leu Leu
                1               5                  10 ctc ctc aca gtg ctt aca gtt gtt aca ggt tct ggt cat gca agc tct      159
Leu Leu Thr Val Leu Thr Val Val Thr Gly Ser Gly His Ala Ser Ser
    15                  20                  25 acc cca ggt gga gaa aag gag act tcg gct acc cag aga agt tca gtg     207
Thr Pro Gly Gly Glu Lys Glu Thr Ser Ala Thr Gln Arg Ser Ser Val
30                  35                  40                  45 ccc agc tct act gag aag aat gct gtg agt atg acc agc agc gta ctc     255
Pro Ser Ser Thr Glu Lys Asn Ala Val Ser Met Thr Ser Ser Val Leu
                50                  55                  60 tcc agc cac agc ccc ggt tca ggc tcc tcc acc act cag gga cag gat     303
Ser Ser His Ser Pro Gly Ser Gly Ser Ser Thr Thr Gln Gly Gln Asp
            65                  70                  75 gtc act ctg gcc ccg gcc acg gaa cca gct tca ggt tca gct gcc acc     351
Val Thr Leu Ala Pro Ala Thr Glu Pro Ala Ser Gly Ser Ala Ala Thr
        80                  85                  90 tgg gga cag gat gtc acc tcg gtc cca gtc acc agg cca gcc ctg ggc     399
Trp Gly Gln Asp Val Thr Ser Val Pro Val Thr Arg Pro Ala Leu Gly
    95                  100                 105 tcc acc acc ccg cca gcc cac gat gtc acc tca gcc ccg gac aac aag     447
Ser Thr Thr Pro Pro Ala His Asp Val Thr Ser Ala Pro Asp Asn Lys
110                 115                 120                 125 cca gcc ccg ggc tcc acc gcc ccc cca gcc cac ggt gtc acc tcg gcc     495
Pro Ala Pro Gly Ser Thr Ala Pro Pro Ala His Gly Val Thr Ser Ala
                130                 135                 140 ccg gac acc agg ccg gcc ccg ggc tcc acc gcc ccc cca gcc cat ggt     543
Pro Asp Thr Arg Pro Ala Pro Gly Ser Thr Ala Pro Pro Ala His Gly
            145                 150                 155
```

```
                                                    -continued gtc acc tcg gcc ccg gac aac agg ccc gcc ttg ggc tcc acc gcc cct     591
Val Thr Ser Ala Pro Asp Asn Arg Pro Ala Leu Gly Ser Thr Ala Pro
        160                 165                 170 cca gtc cac aat gtc acc tcg gcc tca ggc tct gca tca ggc tca gct     639
Pro Val His Asn Val Thr Ser Ala Ser Gly Ser Ala Ser Gly Ser Ala
    175                 180                 185 tct act ctg gtg cac aac ggc acc tct gcc agg gct acc aca acc cca     687
Ser Thr Leu Val His Asn Gly Thr Ser Ala Arg Ala Thr Thr Thr Pro
190                 195                 200                 205 gcc agc aag agc act cca ttc tca att ccc agc cac cac tct gat act     735
Ala Ser Lys Ser Thr Pro Phe Ser Ile Pro Ser His His Ser Asp Thr
                210                 215                 220 cct acc acc ctt gcc agc cat agc acc aag act gat gcc agt agc act     783
Pro Thr Thr Leu Ala Ser His Ser Thr Lys Thr Asp Ala Ser Ser Thr
            225                 230                 235 cac cat agc acg gta cct cct ctc acc tcc tcc aat cac agc act tct     831
His His Ser Thr Val Pro Pro Leu Thr Ser Ser Asn His Ser Thr Ser
        240                 245                 250 ccc cag ttg tct act ggg gtc tct ttc ttt ttc ctg tct ttt cac att     879
Pro Gln Leu Ser Thr Gly Val Ser Phe Phe Phe Leu Ser Phe His Ile
    255                 260                 265 tca aac ctc cag ttt aat tcc tct ctg gaa gat ccc agc acc gac tac     927
Ser Asn Leu Gln Phe Asn Ser Ser Leu Glu Asp Pro Ser Thr Asp Tyr
270                 275                 280                 285 tac caa gag ctg cag aga gac att tct gaa atg ttt ttg cag att tat     975
Tyr Gln Glu Leu Gln Arg Asp Ile Ser Glu Met Phe Leu Gln Ile Tyr
                290                 295                 300 aaa caa ggg ggt ttt ctg ggc ctc tcc aat att aag ttc agg cca gga    1023
Lys Gln Gly Gly Phe Leu Gly Leu Ser Asn Ile Lys Phe Arg Pro Gly
            305                 310                 315 tct gtg gtg gta caa ttg act ctg gcc ttc cga gaa ggt acc atc aat    1071
Ser Val Val Val Gln Leu Thr Leu Ala Phe Arg Glu Gly Thr Ile Asn
        320                 325                 330 gtc cac gac gtg gag aca cag ttc aat cag tat aaa acg gaa gca gcc    1119
Val His Asp Val Glu Thr Gln Phe Asn Gln Tyr Lys Thr Glu Ala Ala
    335                 340                 345 tct cga tat aac ctg acg atc tca gac gtc agc gtg agt gat gtg cca    1167
Ser Arg Tyr Asn Leu Thr Ile Ser Asp Val Ser Val Ser Asp Val Pro
350                 355                 360                 365 ttt cct ttc tct gcc cag tct ggg gct ggg gtg cca ggc tgg ggc atc    1215
Phe Pro Phe Ser Ala Gln Ser Gly Ala Gly Val Pro Gly Trp Gly Ile
                370                 375                 380 gcg ctg ctg gtg ctg gtc tgt gtt ctg gtt gcg ctg gcc att gtc tat    1263
Ala Leu Leu Val Leu Val Cys Val Leu Val Ala Leu Ala Ile Val Tyr
            385                 390                 395 ctc att gcc ttg gct gtc tgt cag tgc cgc cga aag aac tac ggg cag    1311
Leu Ile Ala Leu Ala Val Cys Gln Cys Arg Arg Lys Asn Tyr Gly Gln
        400                 405                 410 ctg gac atc ttt cca gcc cgg gat acc tac cat cct atg agc gag tac    1359
Leu Asp Ile Phe Pro Ala Arg Asp Thr Tyr His Pro Met Ser Glu Tyr
    415                 420                 425 ccc acc tac cac acc cat ggg cgc tat gtg ccc cct agc agt acc gat    1407
Pro Thr Tyr His Thr His Gly Arg Tyr Val Pro Pro Ser Ser Thr Asp
430                 435                 440                 445 cgt agc ccc tat gag aag gtt tct gca ggt aat ggt ggc agc agc ctc    1455
Arg Ser Pro Tyr Glu Lys Val Ser Ala Gly Asn Gly Gly Ser Ser Leu
                450                 455                 460 tct tac aca aac cca gca gtg gca gcc act tct gcc aac ttg tag        1500
Ser Tyr Thr Asn Pro Ala Val Ala Ala Thr Ser Ala Asn Leu
            465                 470                 475 gggcacgtcg cccgctgagc tgagtggcca gccagtgcca ttccactcca ctcaggttct  1560
```

-continued

```
tcagggccag agccctgca ccctgtttgg gctggtgagc tgggagttca ggtgggctgc   1620
tcacaccgtc cttcagaggc cccaccaatt tctcggacac ttctcagtgt gtggaagctc   1680
atgtgggccc ctgaggctca tgcctgggaa gtgttgtggg gggggctccc aggaggactg   1740
gcccagagag ccctgagata gcggggatcc tgaactggac tgaataaaac gtggtctccc   1800
actg                                                                1804
```

<210> SEQ ID NO 18
<211> LENGTH: 572
<212> TYPE: DNA
<213> ORGANISM: Homo sapiens
<220> FEATURE:
<221> NAME/KEY: CDS
<222> LOCATION: (67)...(572)

<400> SEQUENCE: 18

```
acctctcaag cagccagcgc ctgcctgaat ctgttctgcc ccctccccac ccatttcacc     60 accacc atg aca ccg ggc acc cag tct cct ttc ttc ctg ctg ctg ctc      108
       Met Thr Pro Gly Thr Gln Ser Pro Phe Phe Leu Leu Leu Leu
       1               5                   10 ctc aca gtg ctt aca gct acc aca gcc cct aaa ccc gca aca gtt gtt    156
Leu Thr Val Leu Thr Ala Thr Thr Ala Pro Lys Pro Ala Thr Val Val
15                  20                  25                  30 acg ggt tct ggt cat gca agc tct acc cca ggt gga gaa aag gag act    204
Thr Gly Ser Gly His Ala Ser Ser Thr Pro Gly Gly Glu Lys Glu Thr
                35                  40                  45 tcg gct acc cag aga agt tca gtg ccc agc tct act gag aag aat gct    252
Ser Ala Thr Gln Arg Ser Ser Val Pro Ser Ser Thr Glu Lys Asn Ala
            50                  55                  60 gtg agt atg acc agc agc gta ctc tcc agc cac agc ccc ggt tca ggc    300
Val Ser Met Thr Ser Ser Val Leu Ser Ser His Ser Pro Gly Ser Gly
        65                  70                  75 tcc tcc acc act cag gga cag gat gtc act ctg gcc ccg gcc acg gaa    348
Ser Ser Thr Thr Gln Gly Gln Asp Val Thr Leu Ala Pro Ala Thr Glu
    80                  85                  90 cca gct tca ggt tca gct gcc acc tgg gga cag gat gtc acc tcg gtc    396
Pro Ala Ser Gly Ser Ala Ala Thr Trp Gly Gln Asp Val Thr Ser Val
95                  100                 105                 110 cca gtc acc agg cca gcc ctg ggc tcc acc acc ccg cca gcc cac gat    444
Pro Val Thr Arg Pro Ala Leu Gly Ser Thr Thr Pro Pro Ala His Asp
                115                 120                 125 gtc acc tca gcc ccg gac aac aag cca gcc ccg ggc tcc acc gcc ccc    492
Val Thr Ser Ala Pro Asp Asn Lys Pro Ala Pro Gly Ser Thr Ala Pro
            130                 135                 140 caa gcc cac ggt gtc acc tcg gcc ccg gac acc agg ccg gcc ccg ggc    540
Gln Ala His Gly Val Thr Ser Ala Pro Asp Thr Arg Pro Ala Pro Gly
        145                 150                 155 tcc acc gcc ccc caa gcc cac ggt gtc acc tc                         572
Ser Thr Ala Pro Gln Ala His Gly Val Thr
    160                 165
```

<210> SEQ ID NO 19
<211> LENGTH: 8186
<212> TYPE: DNA
<213> ORGANISM: Homo sapiens
<220> FEATURE:
<221> NAME/KEY: unsure
<222> LOCATION: 6899
<223> OTHER INFORMATION: unknown
<221> NAME/KEY: unsure
<222> LOCATION: 7155

```
<223> OTHER INFORMATION: unknown
<221> NAME/KEY: unsure
<222> LOCATION: 7184
<223> OTHER INFORMATION: unknown
<221> NAME/KEY: unsure
<222> LOCATION: 7957
<223> OTHER INFORMATION: unknown
<221> NAME/KEY: intron
<222> LOCATION: (2997)...(3498)
<223> OTHER INFORMATION: intron 1
<221> NAME/KEY: intron:exon junction
<222> LOCATION: (3498)...(3499)
<223> OTHER INFORMATION: intron 1:exon 2
<221> NAME/KEY: exon
<222> LOCATION: (3508)...(3599)
<223> OTHER INFORMATION: exon 2d
<221> NAME/KEY: exon:intron junction
<222> LOCATION: (3982)...(3983)
<223> OTHER INFORMATION: exon 2a:intron 2a
<221> NAME/KEY: intron:exon junction
<222> LOCATION: (4205)...(4206)
<223> OTHER INFORMATION: intron 2c:exon 3c
<221> NAME/KEY: intron:exon junction
<222> LOCATION: (4259)...(4260)
<223> OTHER INFORMATION: intron 2d:exon 3d
<221> NAME/KEY: exon
<222> LOCATION: (4260)...(4328)
<223> OTHER INFORMATION: exon 3d
<221> NAME/KEY: intron:exon junction
<222> LOCATION: (4632)...(4633)
<223> OTHER INFORMATION: intron 3:exon 4
<221> NAME/KEY: exon
<222> LOCATION: (4914)...(5035)
<223> OTHER INFORMATION: exon 5
<221> NAME/KEY: intron
<222> LOCATION: (5266)...(6293)
<223> OTHER INFORMATION: intron 6

<400> SEQUENCE: 19
gaattcagaa tttagaccc tttggccttg gggtccatcc tggagaccct gaggtctaag      60
ctacagcccc tcagccaacc acagacccett ctctggctcc caaaaggagt tcagtcccag    120
agggtggtca cccaccctte aggatgaga agttttcaag gggtattact caggcactaa     180
ccccaggaaa gatgacagca cattgccata agtttggt tgttttctaa gccagtgcaa      240
ctgcttattt tagggatttt ccgggatagg gtggggaagt ggaaggaatc ggcgagtaga    300
agagaaagcc tggagggtg gaagttaggg atctagggga agtttggctg atttggggat    360
gcgggtgggg gaggtgctgg atggagttaa gtgaaggata gggtgcctga gggaggatgc    420
ccgaagtcct cccagaccca cttactcacg gtggcagcgg cgacactcca gtctatcaaa    480
gatccgccgg gatggagagc caggaggcgg gggctgcccc tgaggtagcg gggaggccgg    540
ggggccgggg ggcggacggg acgagtgcaa tattggcggg ggaaaaaaca acactgcacc    600
gcgtcccgtc cctcccgccc gcccgggccc ggatcccgct ccccaccgcc tgaagccggc    660
ccgacccgga acccgggccg ctggggagtt gggttcacct tggaggccag agagacttgg    720
cgcccggaag caaagggaat ggcaagggg agggggagg gagaacggga gttttgcggag    780 tccagaaggc cgctttccga cgcccggcg ttgcgcgcgc ttgctctttta agtactcaga    840 ctgcgcggcg cgagccgtcc gcatggtgac gcgtgtccca gcaaccgaac tgaatggctg    900
ttgcttggca atgccgggag ttgaggtttg gggccgccca cctagctact cgtgttttct    960
ccggcctgcg agttgggggg ctcccgcctc cccggcccgc tcctgggcgc gctgacgtca   1020
gatgtcccca ccccgcccag cgcctgcccc aagggtctcg ccgcacacaa agctcggcct   1080
cgggcgccgg cgcgcgggcg agagcggtgg tctctcgcct gctgatctga tgcgctccaa   1140
tcccgtgcct cgccgaagtg ttttaaagt gttctttcca acctgtgtct ttggggctga   1200
```

-continued

```
gaactgttttt ctgaatacag gcggaactgc ttccgtcggc ctagaggcac gctgcgactg      1260
cgggacccaa gttccacgtg ctgccgcggc ctgggatagc ttcctcccct cgtgcactgc      1320
tgccgcacac acctcttggc tgtcgcgcat tacgcacctc acgtgtgctt ttgcccccg       1380 ctacgtgcct acctgtcccc aataccactc tgctccccaa aggatagttc tgtgtccgta      1440
aatcccattc tgtcacccca cctactctct gcccccccct tttttgtttt gagacggagc      1500
tttgctctgt cgcccaggct ggagtgcaat ggcgcgatct cggctcactg caacctccgc      1560
ctcccgggtt caagcgattc tcctgcctca gcctcctgag tagctgggt tacagcgccc       1620 gccaccacgc tcggctaatt tttgtagttt ttagtagaga cgaggtttca ccatcttggc      1680
caggctggtc ttgaacccct gaccttgtga tccactcgcc tcggccttcc aaagtgttgg     1740
gattacgggc gtgacgaccg tgccacgcat ctgcctctta agtacataac ggcccacaca     1800
gaacgtgtcc aactccccg cccacgttcc aacgtcctct cccacatacc tcggtgcccc     1860
ttccacatac ctcaggaccc cacccgctta gctccatttc ctccagacgc caccaccacg    1920
cgtcccggag tgccccctcc taaagctccc agccgtccac catgctgtgc gttcctccct   1980
ccctggccac ggcagtgacc cttctctccc gggccctgct tccctctcgc gggctctgct   2040
gcctcactta ggcagcgctg cccttactcc tctccgcccg gtccgagcgg ccctcagct    2100 tcggcgccca gccccgcaag gctcccggtg accactagag ggcgggagga gctcctggcc   2160
agtggtggag agtggcaagg aaggacccta gggttcatcg gagcccaggt ttactccctt    2220
aagtggaaat tcttcccccc actcctcctt ggctttctcc aaggagggaa cccaggctgc   2280
tggaaagtcc ggctgggggg gggactgtgg gttcagggga gaacgggtg tggaacggga    2340 cagggagcgg ttagaagggt ggggctattc cgggaagtgg tgggggagg gagcccaaaa    2400 ctagcaccta gtccactcat tatccagccc tcttatttct cggccgctct gcttcagtgg    2460
acccggggag ggcggggaag tggagtggga gacctagggg tgggcttccc gaccttgctg   2520
tacaggacct cgacctagct ggctttgttc cccatcccca cgttagttgt tgccctgagg    2580
ctaaaactag agcccagggg ccccaagttc cagactgccc ctcccccctc cccggagcc     2640 agggagtggt tggtgaaagg gggaggccag ctggagaaca aacgggtagt caggggttg    2700 agcgattaga gcccttgtac cctacccagg aatggttggg gaggaggagg aagaggtagg   2760
aggtagggga gggggcgggg ttttgtcacc tgtcacctgc tcgctgtgcc tagggcgggc   2820
gggcggggag tgggggggacc ggtataaagc ggtaggcgcc tgtgcccgct ccacctctca   2880
agcagccagc gcctgcctga atctgttctg cccctcccc acccatttca ccaccaccat    2940
gacaccgggc acccagtctc ctttcttcct gctgctgctc ctcacagtgc ttacaggtga   3000
ggggcacgag gtggggagtg ggctgccctg cttaggtggt cttcgtggtc tttctgtggg    3060
ttttgctccc tggcagatgg caccatgaag ttaaggtaag aattgcagac agaggctgcc    3120
ctgtctgtgc cagaaggagg gagaggctaa ggacaggctg agaagagttg cccccaaccc   3180
tgagagtggg taccagggc aagcaaatgt cctgtagaga agtctagggg gaagagagta    3240
gggagaggga aggcttaaga ggggaagaaa tgcagggggcc atgagccaag gcctatgggc   3300
agagagaagg aggctgctgc agggaaggag gcttccaacc cagggggttac tgaggctgcc   3360 cactccccag tcctcctggt attatttctc tggtggccag agcttatatt ttcttcttgc    3420
tcttattttt ccttcataaa gacccaaccc tatgactttta acttcttaca gctaccacag   3480
cccctaaacc cgcaacagtt gttacaggtt ctggtcatgc aagctctacc ccaggtggag    3540
```

```
aaaaggagac ttcggctacc cagagaagtt cagtgcccag ctctactgag aagaatgctg    3600
tgagtatgac cagcagcgta ctctccagcc acagccccgg ttcaggctcc tccaccactc    3660
agggacagga tgtcactctg gccccggcca cggaaccagc ttcaggttca gctgccacct    3720
ggggacagga tgtcacctcg gtcccagtca ccaggccagc cctgggctcc accaccccgc    3780
cagcccacga tgtcacctca gccccggaca caagccagc cccgggctcc accgcccccc     3840
cagcccacgg tgtcacctcg gccccggaca ccaggccggc cccgggctcc accgcccccc    3900
cagcccatgg tgtcacctcg gccccggaca acaggcccgc cttgggctcc accgccccctc   3960 cagtccacaa tgtcacctcg gcctcaggct ctgcatcagg ctcagcttct actctggtgc    4020
acaacggcac ctctgccagg gctaccacaa ccccagccag caagagcact ccattctcaa    4080
ttcccagcca ccactctgat actcctacca cccttgccag ccatagcacc aagactgatg    4140
ccagtagcac tcaccatagc acggtacctc ctctcacctc ctccaatcac agcacttctc    4200
cccagttgtc tactggggtc tctttctttt tcctgtcttt tcacatttca aacctccagt    4260
ttaattcctc tctggaagat cccagcaccg actactacca agagctgcag agagacattt    4320
ctgaaatggt gagtatcggc cttttccttcc ccatgctccc ctgaagcagc catcagaact    4380
gtccacaccc tttgcatcaa gcccgagtcc tttccctctc accccagttt ttgcagattt    4440
ataaacaagg gggttttctg ggcctctcca atattaagtt caggtacagt tctgggtgtg    4500
gacccagtgt ggtggttgga gggttgggtg gtggtcatga ccgtaggagg gactggtgca    4560
cttaaggttg ggggaagagt gctgagccag agctgggacc cgtggctgaa gtgcccattt    4620
ccctgtgacc aggccaggat ctgtggtggt acaattgact ctggccttcc gagaaggtac    4680
catcaatgtc cacgacgtgg agacacagtt caatcagtat aaaacggaag cagcctctcg    4740
atataacctg acgatctcag acgtcagcgg tgaggctact tccctggctg cagccagcac    4800
catgccgggg cccctctcct tccagtgtct gggtccccgc tctttcctta gtgctggcag    4860
cgggaggggc gcctcctctg ggagactgcc ctgaccactg cttttccttt tagtgagtga    4920
tgtgccattt cctttctctg cccagtctgg ggctggggtg ccaggctggg gcatcgcgct    4980
gctggtgctg gtctgtgttc tggttgcgct ggccattgtc tatctcattg ccttggtgag    5040
tgcagtccct ggccctgatc agagcccccc ggtagaaggc actccatggc ctgccataac    5100
ctcctatctc cccaggctgt ctgtcagtgc cgccgaaaga actacgggca gctggacatc    5160
tttccagccc gggataccta ccatcctatg agcgagtacc ccacctacca cacccatggg    5220
cgctatgtgc cccctagcag taccgatcgt agccccctatg agaaggtgag attggcccca    5280
caggccaggg gaagcagagg gttttggctgg gcaaggattc tgaaggggt acttggaaaa    5340 cccaaagagc ttggaagagg tgagaagtgg cgtgaagtga gcagggagg gcctggcaag    5400 gatgaggggc agaggtcaga ggagtttttgg gggacaggcc tggaggaga ctatggaaga    5460 aagggccctc aagagggagt ggccccactg ccagaattcc taaaaagatc attggccgtc    5520
cacattcatg ctggctggcg ctggctgaac tggtgccacc gtggcagttt tgttttgttt    5580
tgcttttttg cacccagagg caaaatgggt ggagcactat gccaggggga gcccttcccg    5640
aggagtccag gggtgagcct ctgtgatccc ctaatcaatc tcctaggaat ggagggtaga    5700
ccgagaaaag gctggcatag ggggagtcag tttcccaggt agaagcaaga agaagtgtca    5760
gcagaccagg tgagcgtggg tgccagtggg gttcttggga gcttcaagga agcaaggaac    5820
gctccctcct tcctctcctg gtctttctct atgggaccta gtaaataatt actgcagcca    5880
cctgaggctg gaaaaccact ccaggtgggg gaggagagag tttagttttc ttgctcctat    5940
```

-continued

```
tttcctcctc ctggagacct ccctctctcg gctttacaaa gacacagata caccccgccc      6000
cccaaaacac acacacacac acacacacac acacctcctt aggctggaac agcagagaat      6060
ggagggacaa gggggctgat tagagccaag aagagggagt gaaggagagc agagggagga      6120
gggcagccct gtttacagtc acctggctgg tggggtggca ggtgctctct ctgaattaac      6180
cctttgagag ctgccagga ctctggactg attaccccag cctggggtgg catccagggg       6240
ctctaggagg taccttttgc tcctcaccct ggatctcttt tccttccacc caggtttctg      6300
caggtaatgg tggcagcagc ctctcttaca caaacccagc agtggcagcc acttctgcca      6360
acttgtaggg gcacgtcgcc cgctgagctg agtggccagc cagtgccatt ccactccact      6420
caggttcttc agggccagag cccctgcacc ctgtttgggc tggtgagctg ggagttcagg      6480
tgggctgctc acacgtcctt cagaggcccc accaatttct cggacacttc tcagtgtgtg     6540
gaagctcatg tgggccctg aggctcatgc ctggaagtg ttgtggtggg ggctcccagg        6600
aggactggcc cagagagccc tgagatagcg gggatcctga actggactga ataaaacgtg     6660
gtctcccact ggcgccaact tctgatcttt catctgtgac ccgtgggcag cagggcgtca     6720
gaatgtgtgt gaggggggctg ggggaggaga cagggaggcc aggaggcagt aaggagcgag    6780
tttgtttgag aagcaggaga tgtgaggagg aggtgacatt ggggagtagg ggtggcctga     6840
ggagccacct ctggctaacc ctggcagcac aagaggaagg aggaaacgaa acccaggcng     6900
gctttggagg gctagcgtga ctgggctccg tgactgagct ctgtgtgcca gtggctctcc     6960
cctctcctcg cctggcccac gccctccttg ccctggcat ggtgcccccc aggtggctct      7020
attcttagct gtccgggtgt gaagtaaatc cttgggcagt gataacagcc cagagtcaac     7080
agggttgaga taagcagagg ctgggtcaga tccggggcgct ggcaccaggc ccagccccct    7140
ccctgacccc ggctncccca ccagcctgct gcccctgggg tggnctccac aacaccctgg    7200
gaatggggaa gtggttctgg ttccctgacc cctttggccc aggcacgttg cctgtccctc     7260
gaccgcattc ccccagggcc tgtgctgcag gcctggaagc cctgattggg gcctgccacc     7320
agcagccaga gagctatgtt ccctggcagc tgtgatcgc tcaggccggg ccaggacacg       7380
tgtggcagga ggcttagagc acctgcctgg ggccttcctc tctcaggcac cagatccatt     7440
ggttgctcct gcctagaacc acagcctagc accctgctc cctcccgcct accacaccca       7500
gcacagaaac tcacaggaat gattgcgctc agggaaggca gagatgtgcc tggcatcaca     7560
gtttattgtt tataaaccat gacaataaca gctgttgctc agcacaggcc tagcagagcc     7620
cactgcaggg ggacggcagc gggcaccaga ggccttgcct ggcccaaccc aatgggaaca     7680
cccagactca gctgggtccc caaggagac ttggcacatt ggcatgggtg tgggacaggt      7740
aaagcatgca agaggggaa gagggacata aggggcatgc ggctgcgggg tgttgggacc     7800
caaataaata aagcaggatg acagggtccc cttcccctca ccaggaatgc ctgacagcgt     7860
ccagccccaa agcctgcctg tcccaaggct gtagttcagc atcaacaggg cagggagctt     7920
ggcagggcaa gggcagagct ggagatcatg cccagtnttc caggtgccct ccctcccaat     7980
cagcctgggg ggcacaggac agggatggag aagggctct ctccatggct tgggtaacat      8040
gccaaaggca ggtcataggg cagactcagt ggggtgggg gcctggctaa caagcaatgg      8100
agagaacggg ggccatccag agaggttggc agaagagagc ccctgggtca agagaaact     8160 ttggggaaga caagacacgg gagaag                                          8186
```

<210> SEQ ID NO 20

-continued

```
<211> LENGTH: 730
<212> TYPE: DNA
<213> ORGANISM: Homo sapiens
<220> FEATURE:
<221> NAME/KEY: CDS
<222> LOCATION: (26)...(718)

<400> SEQUENCE: 20 cctcccccacc catttcacca ccacc atg aca ccg ggc acc cag tct cct ttc      52
                              Met Thr Pro Gly Thr Gln Ser Pro Phe
                                1               5 ttc ctg ctg ctg ctc ctc aca gtg ctt aca gtt gtt aca ggt tct ggt      100
Phe Leu Leu Leu Leu Leu Thr Val Leu Thr Val Val Thr Gly Ser Gly
 10                  15                  20                  25 cat gca agc tct acc cca ggt gga gaa aag gag act tcg gct acc cag      148
His Ala Ser Ser Thr Pro Gly Gly Glu Lys Glu Thr Ser Ala Thr Gln
                 30                  35                  40 aga agt tca gtg ccc agc tct act gag aag aat gct atc cca gca ccg      196
Arg Ser Ser Val Pro Ser Ser Thr Glu Lys Asn Ala Ile Pro Ala Pro
             45                  50                  55 act act acc aag agc tgc aga gag aca ttt ctg aaa tgg cca gga tct      244
Thr Thr Thr Lys Ser Cys Arg Glu Thr Phe Leu Lys Trp Pro Gly Ser
         60                  65                  70 gtg gtg gta caa ttg act ctg gcc ttc cga gaa ggt acc atc aat gtc      292
Val Val Val Gln Leu Thr Leu Ala Phe Arg Glu Gly Thr Ile Asn Val
 75                  80                  85 cac gac gtg gag aca cag ttc aat cag tat aaa acg gaa gca gcc tct      340
His Asp Val Glu Thr Gln Phe Asn Gln Tyr Lys Thr Glu Ala Ala Ser
 90                  95                 100                 105 cga tat aac ctg acg atc tca gac gtc agc gtg agt gat gtg cca ttt      388
Arg Tyr Asn Leu Thr Ile Ser Asp Val Ser Val Ser Asp Val Pro Phe
                110                 115                 120 cct ttc tct gcc cag tct ggg gct ggg gtg cca ggc tgg ggc atc gcg      436
Pro Phe Ser Ala Gln Ser Gly Ala Gly Val Pro Gly Trp Gly Ile Ala
            125                 130                 135 ctg ctg gtg ctg gtc tgt gtt ctg gtt gcg ctg gcc att gtc tat ctc      484
Leu Leu Val Leu Val Cys Val Leu Val Ala Leu Ala Ile Val Tyr Leu
        140                 145                 150 att gcc ttg gct gtc tgt cag tgc cgc cga aag aac tac ggg cag ctg      532
Ile Ala Leu Ala Val Cys Gln Cys Arg Arg Lys Asn Tyr Gly Gln Leu
155                 160                 165 gac atc ttt cca gcc cgg gat acc tac cat cct atg agc gag tac ccc      580
Asp Ile Phe Pro Ala Arg Asp Thr Tyr His Pro Met Ser Glu Tyr Pro
170                 175                 180                 185 acc tac cac acc cat ggg cgc tat gtg ccc cct agc agt acc gat cgt      628
Thr Tyr His Thr His Gly Arg Tyr Val Pro Pro Ser Ser Thr Asp Arg
                190                 195                 200 agc ccc tat gag aag gtt tct gca ggt aat ggt ggc agc agc ctc tct      676
Ser Pro Tyr Glu Lys Val Ser Ala Gly Asn Gly Gly Ser Ser Leu Ser
            205                 210                 215 tac aca aac cca gca gtg gca gcc act tct gcc aac ttg tag gggcacgtcg  728
Tyr Thr Asn Pro Ala Val Ala Ala Thr Ser Ala Asn Leu
        220                 225                 230 cc                                                                   730

<210> SEQ ID NO 21
<211> LENGTH: 177
<212> TYPE: DNA
<213> ORGANISM: Homo sapiens
<220> FEATURE:
<221> NAME/KEY: CDS
<222> LOCATION: (74)...(177)
```

<400> SEQUENCE: 21
ccgctccacc tctcaagcag ccagcgcctg cctgaatctg ttctgccccc tccccaccca      60
tttcaccacc acc atg aca ccg ggc acc cag tct cct ttc ttc ctg ctg       109
            Met Thr Pro Gly Thr Gln Ser Pro Phe Phe Leu Leu
              1               5                  10 ctg ctc ctc aca gtg ctt aca ggt gga gaa aag gag act tcg gct acc      157
Leu Leu Leu Thr Val Leu Thr Gly Gly Glu Lys Glu Thr Ser Ala Thr
         15                  20                  25 cag aga agt tca gtg ccc ag                                           177
Gln Arg Ser Ser Val Pro
         30

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
gaacagattc aagcagccag                                                 20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
cccggtgtca tggtggtggt                                                 20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
gtgcccggtg tcatggtggt                                                 20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
gaaaggagac tgggtgcccg                                                 20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
ctgtaacaac tgtaagcact                                                 20

<210> SEQ ID NO 27

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
acctgtaaca actgtaagca                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tcagtagagc tgggcactga                                              20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
gcattcttct cagtagagct                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
agcattcttc tcagtagagc                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
tggtcatact cacagcattc                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
ctgctggtca tactcacagc                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
```
gctggagagt acgctgctgg                                            20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
tgggaccgag gtgacatcct                                            20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gtgacattgt ggactggagg                                            20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
gaggtgacat tgtggactgg                                            20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
tgaggccgag gtgacattgt                                            20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
gtggtaggag tatcagagtg                                            20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
gcaagggtgg taggagtatc                                            20

<210> SEQ ID NO 40
<211> LENGTH: 20
<212> TYPE: DNA

-continued

<213> ORGANISM: Artificial Sequence
<220> FEATURE:
<223> OTHER INFORMATION: Antisense Oligonucleotide

<400> SEQUENCE: 40
ggcatcagtc ttggtgctat 20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide
<400> SEQUENCE: 41
gagaccccag tagacaactg 20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
tcttccagag aggaattaaa 20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
aatgtctctc tgcagctctt 20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
tcagaaatgt ctctctgcag 20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
tctgcaaaaa catttcagaa 20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
gtttataaat ctgcaaaaac 20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
attggagagg cccagaaaac                                        20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
taatattgga gaggcccaga                                        20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
gaacttaata ttggagaggc                                        20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
agatcctggc ctgaacttaa                                        20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
cacagatcct ggcctgaact                                        20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
acgtcgtgga cattgatggt                                        20

<210> SEQ ID NO 53
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 53
gttatatcga gaggctgctt                                               20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
atcgtcaggt tatatcgaga                                               20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
gcacatcact cacgctgacg                                               20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
ggcagagaaa ggaaatggca                                               20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gacagacagc caaggcaatg                                               20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
ctgcccgtag ttctttcggc                                               20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
tggaaagatg tccagctgcc                                               20
```

```
<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
gctacgatcg gtactgctag                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
aggctgctgc caccattacc                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
aagttggcag aagtggctgc                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
ctacaagttg gcagaagtgg                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
acgtgcccct acaagttggc                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
gctcagaggg cgacgtgccc                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 66
ctggccactc agctcagagg                    20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
actggctggc cactcagctc                    20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
ggaatggcac tggctggcca                    20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
ggagtggaat ggcactggct                    20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
aggaattaaa agcattcttc                    20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
cagtagacaa agcattcttc                    20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
gacagacagc catttcagaa                    20

<210> SEQ ID NO 73
<211> LENGTH: 20

-continued

```
<212> TYPE: DNA
<213> ORGANISM: Artificial Sequence
<220> FEATURE:
<223> OTHER INFORMATION: Antisense Oligonucleotide

<400> SEQUENCE: 73
catcactcac tgaacttaat                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tttgggtttt ccaagtaccc                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
catagtctcc tcccaggcct                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
cattttgcct ctgggtgcaa                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
cagccccaga catttcagaa                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ttctctctgc ccataggcct                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
```

```
gggtctttat gaaggaaaaa                                              20
```

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80

```
acatcactca catttcagaa                                              20
```

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81

```
accacgtttt attcagtcca                                              20
```

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82

```
gctgtggtag ctgtaagcac                                              20
```

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83

```
gtgctgggat agcattcttc                                              20
```

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84

```
agagtcaatt gtaccaccac                                              20
```

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85

```
ttttctccac ctgtaagcac                                              20
```

<210> SEQ ID NO 86
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 86
cctgtaacaa ctgttgcggg                                          20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
tgaccagaac ctgtaacaac                                          20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
tctccttttc tccacctggg                                          20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ctcagtagag ctgggcactg                                          20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
tcatactcac agcattcttc                                          20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
agagcctgag gccgaggtga                                          20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
gaccccagta gacaactggg                                          20
```

```
<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
aggaattaaa ctggaggttt                                              20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
gtgctgggat cttccagaga                                              20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
atcctggcct ggtcacaggg                                              20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
cagccccaga ctgggcagag                                              20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97 ggccccttc ttccatagtc                                               20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
ccacctggag tggttttcca                                              20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 99
aaagccgaga gagggaggtc                                                     20

<210> SEQ ID NO 100
<211> LENGTH: 336
<212> TYPE: DNA
<213> ORGANISM: Homo sapiens
<220> FEATURE:

<400> SEQUENCE: 100
accaccacca tgacaccggg cacccagtct cctttcttcc tgctgctgct cctcacagtg         60
cttacagcta ccacagcccc taaacccgca acagttgtta caggttctgg tcatgcaagc       120
tctaccccag gtggagaaaa ggagacttcg gctacccaga gaagttcagt gcccagctct       180
actgagaaga atgctgtgag tatgaccagc agcgtactct ccagccacag ccccggttca       240
ggctcctcca ccactcaggg acaggatgtc actctggccc cggccacgga accagcttca       300
ggttcagctg ccacctgggg acaggatgtc acctcg                                 336

<210> SEQ ID NO 101
<211> LENGTH: 518
<212> TYPE: DNA
<213> ORGANISM: Homo sapiens
<220> FEATURE:

<400> SEQUENCE: 101
gcgcctgcct gaatctgttc tgcccccctcc ccacccattt caccaccacc atgacaccgg        60
gcacccagtc tcctttcttc ctgctgctgc tcctcacagt gcttacagct accacagccc       120
ctaaacccgc aacagttgtt acaggttctg gtcatgcaag ctctacccca ggtggagaaa       180
aggagacttc ggctacccag agaagttcag tgcccagctc tactgagaag aatgctgtga       240
gtatgaccag cagcgtactc tccagccaca gccccggttc aggctcctcc accactcagg       300
gacaggatgt cactctggcc ccggccacgg aaccagcttc aggttcagct gccacctggg       360
gacaggatgt cacctcggtc ccagtcacca ggccagccct gggctccacc accccgccag       420
cccacgatgt cacctcagcc ccggacaaca agccagcccc gggctccacc gcccccccag       480
cccacggtgt cacctcggcc ccggacacca ggccggcc                               518

<210> SEQ ID NO 102
<211> LENGTH: 3343
<212> TYPE: DNA
<213> ORGANISM: Homo sapiens
<220> FEATURE:

<400> SEQUENCE: 102
gagctcctgg ccagtggtgg agagtggcaa ggaaggaccc tagggttcat cggagcccag         60
gtttactccc ttaagtggaa atttcttccc ccactcccct ccttggcttt ctccaaggag       120
ggaaccccag gctgctggaa agtccggctg ggcggggac tgtgggtttc agggtagaac         180
tgcgtgtgga acgggacagg gagcggttag aagggtgggg ctattccggg aagtggtggt       240
gggggggaggg agcccaaaac tagcacctag tccactcatt atccagccct cttatttctc       300
ggccgcctct gcttcagtgg acccggggag ggcggggaag tggagtggga gacctagggg       360
tgggcttccc gaccttgctg tacaggacct cgacctagct ggctttgttc cccatcccca       420
gttagttgtt gccctgaggc taaaactaga gcccaggggc cccaagttcc agactgcccc       480

-continued

| | |
|---|---|
| tcccccctcc cccggagcca gggagtggtt ggtgaaaggg ggaggccagc tggagaagaa | 540 |
| acgggtagtc aggggttgca gcattagagc ccttgtagcc ctagcccagg aatggttgga | 600 |
| gagagaagag tagagtaggg aggggggttt gtcacctgtc acctgctcgg ctgtgcctag | 660 |
| ggcgggcggg ggggagtggg gggaccggta taaagcggta ggcgcctgtg cccgctccac | 720 |
| ctctcaagca gccagcgcct gcctgaatct gttctgcccc ctccccaccc atttcaccac | 780 |
| caccatgaca ccgggcaccc agtctccttt cttcctgctg ctgctcctca cagtgcttac | 840 |
| aggtgagggg cacgaggtgg ggagtgggct gccctgctta ggtggtcttc gtggtctttc | 900 |
| tgtgggtttt gctccctggc agatggcacc agaagttaag gtaagaattg cagacagagg | 960 |
| ctgccctgtc tgtgccagaa ggaggggagag gctaaggaca ggctgagaag agttgccccc | 1020 |
| aaccctgaga gtgggtacca ggggcaagca aatgtcctgt agagaagtct aggggggaaga | 1080 |
| gagtagggag agggaaggct taagagggga agaaatgcag gggccatgag ccaaggccta | 1140 |
| tgggcagaga gaaggaggct gctgcaggaa ggaggcggcc aacccagggg ttactgaggc | 1200 |
| tgcccactcc ccagtcctcc tggtattatt tctctggtgg ccaggcttat attttcttct | 1260 |
| tgctcttatt tttccttcat aaagacccaa ccctatgact ttaacttctt acagctacca | 1320 |
| cagcccctgg gccgcaaca gttgttacag gttctggtca tgcaagctct accccaggtg | 1380 |
| gagaaaagga gacttcggct acccagagaa gttcagtgcc cagctctact gagaagaatg | 1440 |
| ctgtgagtat gaccagcagc gtactctcca gccacagccc cggttcaggc tcctccacca | 1500 |
| ctcagggaca ggatgtcact ctggccccgg ccacggaacc agcttcaggt tcagctgcca | 1560 |
| cctggggaca ggatgtcacc tcggtccag tcaccaggcc agccctgggc tccaccaccc | 1620 |
| cgccagccca cgatgtcacc tcagccccgg acaacaagcc agccccgggc tccaccgccc | 1680 |
| ccccagccca gggtgtcacc tcggccccgg agaccaggcc gccccgggc tccaccgccc | 1740 |
| ccccagccca tggtgtcacc tcggcgccgg acaacaggcc cgccttggcg tccaccgccc | 1800 |
| ctccagtcca caatgtcacc tcggcctcag gctctgcatc aggctcagct tctactctgg | 1860 |
| tgcacaacgg cacctctgcc agggctacca caaccccagc cagcaagagc actccattct | 1920 |
| caattcccag ccaccactct gatactccta ccaccctttgc cagccatagc accaagactg | 1980 |
| atgccagtag cactcaccat agcacggtac ctcctctcac ctcctccaat cacagcactt | 2040 |
| ctccccagtt gtctactggg gtctctttct ttttcctgtc ttttcacatt tcaaacctcc | 2100 |
| agtttaattc ctctctggaa gatcccagca ccgactacta ccaagagctg cagagagaca | 2160 |
| tttctgaaat ggtgagtatc ggcctttcct tccccatgct cccctgaagc agccatcaga | 2220 |
| actgtccaca ccctttgcat caagcctgag tcctttccct ctcaccccag tttttgcaga | 2280 |
| tttataaaca aggggggtttt ctgggcctct ccaatattaa gttcaggtac agttctgggt | 2340 |
| gtggacccag tgtggtggtt ggaggggtgg gtggtggtca tgagccgtag ggagggactg | 2400 |
| gtgcacttaa ggttgggggga agagtgctga gccagagctg ggacccgtgg ctgaagtgcc | 2460 |
| catttccctg tgaccaggcc aggatctgtg gtggtacaat tgactctggc cttccgagaa | 2520 |
| ggtaccatca atgtccacga cgtggagaca cagttcaatc agtataaaac ggaagcagcc | 2580 |
| tctcgatata acctgacgat ctcaagacgt cagcggtgag gctacttccc tgctgcagcc | 2640 |
| agcaccatgc cggggcccct ctccttccag tgtctgggtc ccgctctttt ccttagtgct | 2700 |
| ggcagcggga gggcgcctc ctctgggaga ctgccctgac cactgctttt cctttagtg | 2760 |
| agtgatgtgc catttccttt ctctgaccag tctggggct gggtgccagg ctgggcatc | 2820 |
| gcgctgctgg tgctggtctg tgttctggtt gcgctggcca ttgtctatct cattgccttg | 2880 |

```
gtgagtgcag tccctggccc tgatcagagc ccccggtag aaggcactcc atggcctgcc      2940
ataacctcct atctccccag gctgtctgtc agtgccgccg aaagaactac gggcagctgg      3000
acatctttcc agcccgggat acctaccatc ctatgagcga gtaccccacc taccacaccc      3060
atgggcgcta tgtgccccta gcagtaccga tcgtagcccc tatgagaagg tgagattggg      3120
ccccacaggc aggggaagca gagggtttgg ctgggcaagg attctgaagg gggtacttgg      3180
aaaacccaaa gagcttggaa gaggtgagaa gtggcgtgaa gtgagcaggg gagggctggc      3240
aaggatgagg ggcagaggtc agaggagttt tgggggacag gcctgggagg agactatgga      3300 agaaagggc ccctcaaaag ggagtgcccc actgccagaa ttc                        3343
```

<210> SEQ ID NO 103
<211> LENGTH: 859
<212> TYPE: DNA
<213> ORGANISM: Homo sapiens
<220> FEATURE:

<400> SEQUENCE: 103

```
cctccccacc catttcacca ccaccatgac accgggcacc cagtctcctt tcttcctgct       60
gctgctcctc acagtgctta cagttgttac aggttctggt catgcaagct ctaccccagg      120
tggagaaaag gagacttcgg ctacccagag aagttcagtg cccagctcta ctgagaagaa      180
tgctttgtct actggggtct cttttctttt cctgtctttt cacatttcaa acctccagtt      240
taattcctct ctggaagatc ccagcaccga ctactaccaa gagctgcaga gagacatttc      300
tgaaatgttt ttgcagattt ataaacaagg gggttttctg ggcctctcca atattaagtt      360
caggccagga tctgtggtgg tacaattgac tctggccttc cgagaaggta ccatcaatgt      420
ccacgacgtg gagacgcagt tcaatcagta taaaacggaa gcagcctctc gatataacct      480
gacgatctca gacgtcagcg tgagtgatgt gccatttcct ttctctgccc agtctggggc      540
tggggtgcca ggctggggca tcgcgctgct ggtgctggtc tgtgttctgg ttgcgctggc      600
cattgtctat ctcattgcct tggctgtctg tcagtgccgc cgaaagaact acgggcagct      660
ggacatcttt ccagcccggg atacctacca tcctatgagc gagtacccca cctaccacac      720
ccatgggcgc tatgtgcccc tagcagtacg atcgtagccc ctatgaga cggtttctgc       780 aggtaatggt ggcagcagcc tctcttacac aaacccagca gtggcagcca cttctgccaa      840
cttgtagggg cacgtcgcc                                                   859
```

<210> SEQ ID NO 104
<211> LENGTH: 204
<212> TYPE: DNA
<213> ORGANISM: Homo sapiens
<220> FEATURE:

<400> SEQUENCE: 104

```
ccgctccacc tctcaagcag ccagcgcctg cctgaatctg ttctgccccc tccccaccca       60
tttcaccacc accatgacac cgggcaccca gtctcctttc ttcctgctgc tgctcctcac      120
agtgcttaca ggttctggtc atgcaagctc taccccaggt ggagaaaagg agacttcggc      180
tacccagaga agttcagtgc ccag                                             204
```

<210> SEQ ID NO 105
<211> LENGTH: 556
<212> TYPE: DNA
<213> ORGANISM: Homo sapiens
<220> FEATURE:

<221> NAME/KEY: misc_feature
<222> LOCATION: 5
<223> OTHER INFORMATION: n = A,T,C or G

<400> SEQUENCE: 105

| | | | | | |
|---|---|---|---|---|---|
| acggnggaag | agagtaggga | gagggaaggc | ttaagagggg | aagaaatgca | ggggccatga | 60 |
| gccaaggcct | atgggcagag | agaaggaggc | tgctgcaggg | aaggaggcgg | ccaacccagg | 120 |
| ggttactgag | gctgcccact | ccccagtcct | cctggtatta | tttctctggt | ggccagagct | 180 |
| tatattttct | tcttgctctt | attttccttt | cataaagacc | caaccctatg | actttaactt | 240 |
| cttacagcta | ccacagcccc | taaacccgca | acagttgtta | cgggttctgg | tcatgcaagc | 300 |
| tctaccccag | gtggagaaaa | ggagacttcg | gctacccaga | gaagttcagt | gcccagctct | 360 |
| actgagaaga | atgctgtgag | tatgaccagc | agcgtactct | ccagccacag | ccccggttca | 420 |
| ggctcctcca | ccactcaggg | acaggatgtc | actctggccc | cggccacgga | accagcttca | 480 |
| ggttcaagct | gccacctggg | acaggatgtc | accttcgtcc | cagtcaccag | gccagccctg | 540 |
| ggctccacca | ccccgc | | | | | 556 |

<210> SEQ ID NO 106
<211> LENGTH: 772
<212> TYPE: DNA
<213> ORGANISM: Homo sapiens
<220> FEATURE:

<400> SEQUENCE: 106

| | | | | | |
|---|---|---|---|---|---|
| gacctctcaa | gcagccagcg | cctgcctgaa | tctgttctgc | cccctcccca | cccatttcac | 60 |
| caccaccatg | acaccgggca | cccagtctcc | tttcttcctg | ctgctgctcc | tcacagtgct | 120 |
| tacagctacc | acagccccta | aacccgcaac | agttgttacg | ggttctggtc | atgcaagctc | 180 |
| taccccaggt | ggagaaaagg | agacttcggc | tacccagaga | agttcagtgc | ccagctctac | 240 |
| tgagaagaat | gcttttaatt | cctctctgga | agatcccagc | accgactact | accaagagct | 300 |
| gcagagagac | atttctgaaa | tgtttttgca | gatttataaa | caaggggtt | ttctgggcct | 360 |
| ctccaatatt | aagttcaggc | caggatctgt | ggtggtacaa | ttgactctgg | ccttccgaga | 420 |
| aggtaccatc | aatgtccacg | acgtggagac | acagttcact | cagtataaac | ggaagcagcc | 480 |
| tctcgatata | acctgacgat | ctcagacgtc | agcgtgagtg | atgtgccatt | tccttttctc | 540 |
| tgcccagtct | ggggctgggg | ttgccaggct | ggggcatcgc | ggctgctggt | gctgggtctg | 600 |
| tgtcctggtt | gcgctggcca | ttgtctatct | cattgccttg | cgctgtcctg | tcagtgccgc | 660 |
| ggacagaaca | cgggccgctg | gacctctttc | ccgcccggga | tacctacatc | ctttgagggg | 720 |
| agtccccact | acacaccatg | ggggattgt | gcccccttagc | gttccgatcg | ac | 772 |

<210> SEQ ID NO 107
<211> LENGTH: 635
<212> TYPE: DNA
<213> ORGANISM: Homo sapiens
<220> FEATURE:
<221> NAME/KEY: misc_feature
<222> LOCATION: 472, 482
<223> OTHER INFORMATION: n = A,T,C or G

<400> SEQUENCE: 107

| | | | | | |
|---|---|---|---|---|---|
| ggctggggtg | ccaggctggg | gcatcgcgct | gctggtgctg | gtctgtgttc | tggttgcgct | 60 |
| ggccattgtc | tatctcattg | ccttggctgt | ctgtcagtgc | cgccgaaaga | actacgggca | 120 |

-continued

```
gctggacatc tttccagccc gggataccta ccatcctatg agcgagtacc ccacctacca      180
cacccatggg cgctatgtgc cccctagcag taccgatcgt agccctatg agaaggtgag       240 attgggcccc acaggccagg ggaagcagag ggtttggctg ggcaaggatt ctgaagggg       300 tacttggaaa acccaaagag cttggaagag gtgagaagtg gcgtgaagtg agcaggggag      360
ggcctggcaa ggatgagggg cagaggtcag aggagttttg ggggacaggc ctgggaggag      420
actatggaag aaagggccc tcaagaggga gtggcccccac tgccagaatt cntaaaagat     480
cnttggccgt ccacattcat gctggctggc gctggctgaa ctggtgccac cgtggcagtt     540
ttgttttgtt ttgctttttt gcacccagag gcaaaatggg tggagcacta tgcccagggg    600
agcccttccc gaggagtcca aggggtgagc ttttg                                635
```

ANTISENSE MODULATION OF MUCIN 1, TRANSMEMBRANE EXPRESSION

FIELD OF THE INVENTION

The present invention provides compositions and methods for modulating the expression of mucin 1, transmembrane. In particular, this invention relates to compounds, particularly oligonucleotides, specifically hybridizable with nucleic acids encoding mucin 1, transmembrane. Such compounds have been shown to modulate the expression of mucin 1, transmembrane.

BACKGROUND OF THE INVENTION

Mucins are high-molecular-weight, heavily glycosylated proteins found in milk, mammary gland and lactating tissue, as well as other simple secretory epithelial tissues. Mucins are constituents of the physical and biological barrier in protective mucous of respiratory, ductal and glandular epithelia. In humans, at least 10 distinct epithelial mucin core polypeptide genes have been identified (MUC1, MUC2, MUC3, MUC4, MUC5AC, MUC5B, MUC6, MUC7, MUC8, and MUC9), and these mucins share the common features of bearing tandem repeat domains rich in proline, serine and threonine residues and forming O-glycans, with N-acetylgalactosamine linkages at hundreds of sites. Mucins are purported to be the most polymorphic of all biological macromolecules produced by eukaryotic organisms (even more so than immunoglobulin and T cell receptors). Mucin O-glycans serve as epitopes representing blood group and as related genetically polymorphic antigens (Irimura et al., *J. Biochem.* (*Tokyo*), 1999, 126, 975–985).

The highly-glycosylated mucin-type glycoproteins present in human urine and several normal and malignant tissues of epithelial origin are very antigenic, and in searches for epithelial and tumor-associated antigens, a large number of monoclonal antibodies have been produced which bind to the mucins. These antibodies have been used in cancer diagnosis and therapy, as well as to study the expression and variation of the PUM (peanut lectin binding urinary mucins) antigens and to confirm that the PUM locus, a highly-polymorphic "minisatellite" region of the genome, encodes a mammary mucin (Karlsson et al., *Ann. Hum. Genet.*, 1983, 47, 263–269; Swallow et al., *Nature*, 1987, 328, 82–84). A full-length cDNA encoding mucin 1, transmembrane (also known as MUC1, episialin, epitectin, polymorphic epithelial mucin, PEM, peanut-reactive urinary mucin, PUM, epithelial membrane antigen, EMA, PAS-0, NCRC11, H23 antigen, H23-ETA transmembrane antigen, DF3 antigen, and CD227) was deduced from overlapping clones isolated from a cDNA library constructed from the BT20 breast cancer cell line. The mucin 1, transmembrane gene encodes a protein with three distinct regions: a signal peptide and degenerate tandem repeats at the N-terminus; the major portion of the protein comprising 60-base pair repeats which form a variable number tandem repeats (VNTR) region, length varying with the individual; and a C-terminus comprising degenerate tandem repeats, a unique transmembrane sequence and a cytoplasmic tail (Gendler et al., *J. Biol. Chem.*, 1990, 265, 15286–15293). This VNTR region is expressed, and it accounts for the polymorphism observed in both the mucin 1, transmembrane gene and its protein product.

Concurrently, a monospecific polyclonal antiserum against deglycosylated human pancreatic tumor mucin was used to clone a mucin cDNA from an expression library prepared from the HPAF pancreatic tumor cell line (Lan et al., *J. Biol. Chem.*, 1990, 265, 15294–15299). This cDNA was found to be distinct from intestinal mucin, but to be 99% homologous to the human breast mucin CDNA cloned by Gendler, et al., leading to the suggestion that, although the native forms of the pancreatic and breast mucin proteins are distinct in size and degree of glycosylation, factors other than its primary sequence determine these characteristics, and the core protein (referred to as apomucin by Lan et al.) is encoded by same gene, hereafter referred to as mucin 1, transmembrane. Northern analyses of RNA from pancreatic and breast adenocarcinoma and colon tumor cell lines revealed a 4.4-kilobase (kb) mucin 1, transmembrane mRNA in 5 of 7 pancreatic tumor cell lines and two of two breast tumor cell lines, whereas no transcript was detected in the mucin-producing colon tumor lines tested. In addition to the 4.4 kb transcript, a larger mRNA with heterogeneous sizes greater than 7 kb was observed in the Colo 357 pancreatic cell line (Lan et al., *J. Biol. Chem.*, 1990, 265, 15294–15299).

A series of human-rodent somatic cell hybrids were used to map the PUM locus to human chromosome 1, and by in situ hybridization, the mucin 1, transmembrane gene was more finely mapped to the 1q21–24 region (Swallow et al., *Ann. Hum.Genet.*, 1987, 51, 289–294). The gene coding for Duffy blood group FY is closely linked to this same region (Swallow et al., *Ann. Hum. Genet.*, 1988, 52, 269–271) and close linkage of mucin 1, transmembrane to alpha-spectrin, a major component of the erythrocyte membrane, confirms the position of mucin 1, transmembrane at chromosomal locus 1q21 (Middleton-Price et al., *Ann. Hum. Genet.*, 1988, 52, 273–278).

The extracellular variable tandem repeat domain of mucin 1, transmembrane protein is highly O-glycosylated, with each 20 amino acid repeat bearing five potential glycosylation sites. Aberrant glycosylation has been described in malignancies. Due to the VNTRs, abberant glycosylation, and alternative splicing, a considerable number of mucin 1, transmembrane isoforms have been described. To date, these are: MUC1, the so-called "normal" isoform; MUC1/REP, expressed in cervical cancer; MUC1/A, the "cancer-specific" isoform found in thyroid carcinoma tissue; MUC1/SEC, lacking the transmembrane domain and is a secreted isoform; MUC1/X, MUC1/Y, and MUC1/Z which lack the VNTR region; and two recently identified splice variants, MUC1/C, MUC1/D, expressed in cervical carcinoma (Obermair et al., *Gynecol. Oncol.*, 2001, 83, 343–347).

In contrast to other mucins such as those secreted by goblet cells of the inner lining of the intestine, airway, and reproductive tract, mucin 1, transmembrane is an integral plasma membrane protein localized to the apical surface of polarized epithelial cells, including, but not limited to, the uterus, cervix, and vagina, as well as secretory epithelial cells of the mammary gland (Mather et al., *Cell Tissue Res.*, 2001, 304, 91–101), and to both normal and malignant lung epithelial cells (Griffiths et al., *Dis. Markers*, 1988, 6, 195–202).

The cytoplasmic tail of mucin 1, transmembrane protein is believed to interact with actin filaments of the cytoskeleton, and its relatively large, highly glycosylated extracellular domain may present a physical barrier that protects the cell with anti-invasion characteristics. Mucin 1, transmembrane may help to frustrate infection in the mammary gland (mastitis) and possibly in other sites in the body (such as bladder and kidney infections) by competitively inhibiting the binding of microorganisms. A mucin 1, transmembrane null mouse has been generated, and these knockout mice are predisposed to bacterial conjunctivitis and blepharitis, demonstrating an important role for mucin 1, transmembrane in ocular mucosal defense (Kardon et al., *Invest. Ophthalmol. Vis. Sci.,* 1999, 40, 1328–1335).

Mucin 1, transmembrane may also play a role the immune response, intracellular signaling, and in suppression of cell adhesion or wall-to-wall adherence in lumens and ducts, preventing their closure and preserving the integrity of secretory systems. Tumor cells tend to express mucin 1, transmembrane aberrantly in a non-polarized manner, potentially facilitating their tumor invasion and metastasis to other locations, and consequently, mucin 1, transmembrane may be associated with biologically aggressive tumors and a worse prognosis (Patton et al., *Biochim. Biophys. Acta,* 1995, 1241, 407–423; Rahn et al., *Cancer,* 2001, 91, 1973–1982).

The multiple functions of mucin 1, transmembrane in carcinoma-host interactions are believed to be dependent on its polymorphic nature, particularly its glycosylation status. Many carcinoma-associated markers are glycoproteins whose expression undergoes temporal or spatial regulation, and mucin 1, transmembrane is such a molecule (Rahn et al., *Cancer,* 2001, 91, 1973–1982). Several data suggest that mucin 1, transmembrane plays a role in tumor progression and metastasis: an underglycosylated form of mucin 1, transmembrane is overexpressed in virtually all invasive breast carcinomas; mucin 1, transmembrane is overexpressed in advanced stage tumors and metastatic foci from colon carcinoma; and mucin 1, transmembrane overexpression is inversely correlated with post-surgical survival of renal cell carcinoma patients (Irimura et al., *J. Biochem. (Tokyo),* 1999, 126, 975–985). Expression of mucin 1, transmembrane is up-regulated in ovarian cancer cell lines (Hough et al., *Cancer Res.,* 2000, 60, 6281–6287) and lung adenocarcinomal cell lines (Yu et al., *Oncology,* 1996, 53, 118–126). Thus, mucin 1, transmembrane is a prime candidate for therapeutic strategies targeting this carcinoma associated antigen.

Mucin 1, transmembrane has been used as an immunotherapeutic target to elicit both humoral and cellular immunity. A double transgenic mouse model for pancreatic cancer that overexpresses large amounts of underglycosylated mucin 1, transmembrane protein and spontaneously develops mucin 1, transmembrane-expressing tumors of the pancreas has been used to study the native immune response. These mice raised low-affinity cytotoxic T-lymphocytes (CTLs) specific for mucin 1, transmembrane, and these CTLs can be stimulated to kill mucin 1, transmembrane-expressing cancer cell lines in vitro, and eradicate injectable tumors upon adoptive transfer (Mukherjee et al., *J. Immunol.,* 2000, 165, 3451–3460). Similarly, vaccination of mice with a liposomal formulation that incorporates synthetic mucin 1, transmembrane-based lipopeptide and Lipid A into a 1,2-dipalmitoyl-sn-glycero-3-phosphocholine (DPPC)/cholesterol bilayer resulted in production of interferon-gamma and a peptide-specific immunological response dependent on cholesterol content (Batenjany et al., *Biochim. Biophys. Acta,* 2001, 1514, 280–290). In contrast to the response observed upon immunization of mice, cynomolgus monkeys immunized with a peptide fusion of 5 VNTRs of macaque mucin 1, transmembrane conjugated with oxidized mannan mounted a humoral immune response, but not a CTL autoimmune response (Vaughan et al., *Vaccine,* 2000, 18, 3297–3309).

In human cells, the MA5 monoclonal antibody against mucin 1, transmembrane protein was used to explore the potential of mucin 1, transmembrane to serve as an antigenic target for radioimmunotherapy (RAIT). From these studies, it was concluded that radiolabelled MA5 demonstrated therapeutic potential in a majority of the multiple myeloma (MM) cells tested (Burton et al., *Clin. Cancer Res.,* 1999, 5, 3065s–3072s).

A vector expressing the mucin 1, transmembrane cDNA in the antisense orientation was used to transfect the human pancreatic tumor cell line, Panc 1, (Batra et al., *J. Cell Sci.,* 1991, 100, 841–849) or the carcinogen-induced hamster pancreatic ductal tumor cell line, HP-1 (Batra et al., *Int. J. Pancreatol.,* 1992, 12, 271–283), and produce transgenic pancreatic cell lines. Northern and western blot analyses demonstrated mucin 1, transmembrane mRNA and protein expression in cells transfected with the cDNA in the correct orientation with respect to the promoter, but not in control cells (HP-1 cells transfected with vector alone, or with the mucin 1, transmembrane cDNA in the antisense orientation). Ultrastructural analyses of the mucin 1, transmembrane expressing transgenic human Panc 1 cells demonstrated the formation of dense core granules and increased amounts of rough endoplasmic reticulum, representing morphological evidence of potentially increased secretory activity and cellular differentiation (Batra et al., *J. Cell Sci.,* 1991, 100, 841–849). The integration of human mucin 1, transmembrane in hamster HP-1 cells caused no significant change in the growth rate of HP-1 cells in vitro, but resulted in an enhanced growth rate for xenografts of mucin 1, transmembrane transfected HP-1 cells grown in nude mice (Batra et al., *Int. J. Pancreatol.,* 1992, 12, 271–283).

An antisense oligonucleotide, 21 nucleotides in length, corresponding to a portion of the tandemly repeated sequence was used to as a control in an experiment testing the effect of MUC2 mucin antisense oligonucleotides on the expression of MUC2-related antigens. The effect of this antisense oligonucleotide on mucin 1, transmembrane gene expression was not assessed (Bergeron et al., *J. Biol. Chem.,* 1996, 271, 6933–6940).

A phosphorothioate antisense oligonucleotide, of unspecified sequence and length, was purchased from Biognosik GmbH (Göttingen, Germany) and used to inhibit expression of mucin 1, transmembrane, resulting in induction of E-cadherin-mediated cell adhesion in the YMB-S breast cancer cell line (Kondo et al., *Cancer Res.,* 1998, 58, 2014–2019).

Disclosed and claimed in U.S. Pat. Nos. 5,861,381 and 6,203,795 are a pharmaceutical composition which comprises, as therapeutic agent, the polypeptide recognized by antibody H23 (which recognizes the mucin 1, transmembrane protein) as well as a vaccinia virus into the genome of which a DNA fragment coding for said polypeptide is inserted, said DNA fragment being placed under the control of suitable transcription and translation signals, said polypeptide comprising a sequence repeated n times, n being a number from 1 to 80. Further claimed is a method of treating or preventing a malignancy characterized by malignant tumors that express elevated amounts of the antigen recognized by the H23 antibody comprising administering a therapeutically or prophylactically effective amount of said pharmaceutical composition (Chambon et al., 2001; Chambon et al., 1999).

Disclosed and claimed in European Patent EP1103623 is a nucleic acid fragment comprising at least 17 nucleotide bases the fragment being hybridizable with at least one of a group of sequences representing the tandemly-repeated sequences within mucin 1, transmembrane. Also claimed is a nucleic acid fragment comprising a portion of at least 30 nucleotide bases capable of hybridizing with at least one of said tandemly-repeated sequences, a double stranded DNA fragment comprising antiparallel paired portions having said sequences, said nucleic acid fragments for use in a method of therapy or diagnosis practiced on the human or animal body, an antibody or fragment thereof against a human mucin core protein which antibody or fragment has reduced or substantially no reaction with fully expressed human mucin glycoprotein, human polymorphic epithelial mucin core protein, a polypeptide comprising 5 or more amino acid residues in a sequence corresponding to a portion of mucin 1, transmembrane protein, and a diagnostic or therapeutic method practiced on the human or animal body comprising administering an antibody or fragment thereof, or human polymorphic epithelial mucin core protein (Taylor-Papadimitriou et al., 2001).

To date, investigative strategies aimed at modulating mucin 1, transmembrane function have involved the use of antisense expression vectors, antisense oligonucleotides, and antibodies. Currently, however, there are no known therapeutic agents which effectively inhibit the synthesis of mucin 1, transmembrane.

Consequently, there remains a long felt need for agents capable of effectively inhibiting mucin 1, transmembrane function.

Antisense technology is emerging as an effective means for reducing the expression of specific gene products and may therefore prove to be uniquely useful in a number of therapeutic, diagnostic, and research applications for the modulation of mucin 1, transmembrane expression.

The present invention provides compositions and methods for modulating mucin 1, transmembrane expression, including modulation of variants of mucin 1, transmembrane.

SUMMARY OF THE INVENTION

The present invention is directed to compounds, particularly antisense oligonucleotides, which are targeted to a nucleic acid encoding mucin 1, transmembrane, and which modulate the expression of mucin 1, transmembrane. Pharmaceutical and other compositions comprising the compounds of the invention are also provided. Further provided are methods of modulating the expression of mucin 1, transmembrane in cells or tissues comprising contacting said cells or tissues with one or more of the antisense compounds or compositions of the invention. Further provided are methods of treating an animal, particularly a human, suspected of having or being prone to a disease or condition associated with expression of mucin 1, transmembrane by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding mucin 1, transmembrane, ultimately modulating the amount of mucin 1, transmembrane produced. This is accomplished by providing antisense compounds which specifically hybridize with one or more nucleic acids encoding mucin 1, transmembrane. As used herein, the terms "target nucleic acid" and "nucleic acid encoding mucin 1, transmembrane" encompass DNA encoding mucin 1, transmembrane, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of mucin 1, transmembrane. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding mucin 1, transmembrane. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding mucin 1, transmembrane, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and extronic regions. Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U.S.A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'—$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687, 808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of mucin 1, transmembrane is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding mucin 1, transmembrane, enabling sandwich and other assays to easily be constructed to exploit this fact. Hybridization of the antisense oligonucleotides of the invention with a nucleic acid encoding mucin 1, transmembrane can be detected by means known in the art. Such means may include conjugation of an enzyme to the oligonucleotide, radiolabelling of the oligonucleotide or any other suitable detection means. Kits using such detection means for detecting the level of mucin 1, transmembrane in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable.

Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly (methylcyanoacrylate), poly(ethylcyanoacrylate), poly (butylcyanoacrylate), poly(isobutylcyanoacrylate), poly (isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.
Emulsions The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms,* Lieberman, Rieger and Banker (Eds.), 1988, Marcel Dekker, Inc., New York, N.Y., volume 1, p. 199; Rosoff, in *Pharmaceutical Dosage Forms,* Lieberman, Rieger and Banker (Eds.), 1988, Marcel Dekker, Inc., New York, N.Y., Volume 1, p. 245; Block in *Pharmaceutical Dosage Forms,* Lieberman, Rieger and Banker (Eds.), 1988, Marcel Dekker, Inc., New York, N.Y., volume 2, p. 335; Higuchi et al., in *Remington's Pharmaceutical Sciences,* Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms,* Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms,* Lieberman, Rieger and Banker (Eds.), 1988, Marcel Dekker, Inc., New York, N.Y., volume 1, p. 285; Idson, in *Pharmaceutical Dosage Forms,* Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group:

nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research,* 1994, 11, 1385–1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research,* 1994, 11, 1385; Ho et al., *J. Pharm. Sci.,* 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms,* Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release,* 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion)

were ineffective (Weiner et al., *Journal of Drug Targeting,* 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research,* 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.,* 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside GM1, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.,* 1980, 53, 2778) described liposomes comprising a nonionic detergent, $2C_{12}15G$, that contains a PEG moiety. Illum et al. (*FEBS Lett.,* 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.,* 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta,* 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms,* Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms,* Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems,* 1991, p.92). Each of the above mentioned classes of penetration enhancers are described below in greater detail.

Surfactants

In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems,* 1991, p.92); and perfluorochemical emulsions, such as FC-43. Takahashi et al., *J. Pharm. Pharmacol.,* 1988, 40, 252).

Fatty acids Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems,* 1991, p.92; Muranishi, *Critical Reviews in Therapeutic Drug Carrier Systems,* 1990, 7, 1–33; El Hariri et al., J. Pharm. Pharmacol., 1992, 44, 651–654).

Bile salts The physiological role of bile includes the facilitation of dispersion and absorption of lipids and fat-soluble vitamins (Brunton, Chapter 38 in: Goodman & Gilman's *The Pharmacological Basis of Therapeutics,* 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents

Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al., *J. Control Rel.,* 1990, 14, 43–51).

Non-chelating non-surfactants As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug*

*Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue-can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxy-cyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy,* 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g.

Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabino-furanosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites 2'-(Dimethylaminooxyethoxy) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.639, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in CH$_2$Cl$_2$). Solvent was removed under vacuum and the residue placed on a flash column and eluted with 10% MeOH in CH$_2$Cl$_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over P$_2$O$_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH$_2$Cl$_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropyl-phosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P$_2$O$_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40 mL). Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl)diaminopurine riboside along with a minor amount of the 3'-O-isomer. 2'-O-(2-ethylacetyl)diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'-O—CH$_2$—O—CH$_2$—N(CH$_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O$^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with CH$_2$Cl$_2$ (2×200 mL). The combined CH$_2$Cl$_2$ layers are washed with saturated NaHCO$_3$ solution, followed by saturated NaCl solution and dried over anhydrous sodium sulfate. Evaporation of the solvent followed by silica gel chromatography using MeOH:CH$_2$Cl$_2$:Et$_3$N (20:1, v/v, with 1% triethylamine) gives the title compound.

5'-O-Dimethoxytrityl-2'-O-[2(2-N,N-dimethylaminoethoxy)ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in CH$_2$Cl$_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or U.S. Pat. No. 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, Bioorganic& *Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]--[2'-deoxy]--[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]--[2'-deoxy]--[2'-O-(Methoxyethyl)] Chimeric Phosphorothioate Oligonucleotides

[2'-O-(2-methoxyethyl)]--[2'-deoxy]--[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]--[2'-deoxy Phosphorothioate]--[2'-O-(2-Methoxyethyl) Phosphodiester] Chimeric Oligonucleotides

[2'-O-(2-methoxyethyl phosphodiester]--[2'-deoxy phosphorothioate]--[2'-O-(methoxyethyl)phosphodiester]

chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 5 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.
T-24 Cells The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum ((Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.
A549 Cells The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.
NHDF Cells Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.
HEK Cells Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

MCF7

The human breast carcinoma cell line MCF-7 was obtained from the American Type Culture Collection (Manassas, Va.). MCF-7 cells were routinely cultured in DMEM low glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds

When cells reached 70% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Mucin 1, Transmembrane Expression

Antisense modulation of mucin 1, transmembrane expression can be assayed in a variety of ways known in the art. For example, mucin 1, transmembrane mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are taught in, for example, Ausubel, F. M. et al., *Current Protocols in Molecular Biology,* Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology,* Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of mucin 1, transmembrane can be quantitated in a variety of ways well known in the art, such as immunoprecipitation, Western blot analysis (immunoblotting), ELISA or fluorescence-activated cell sorting (FACS). Antibodies directed to mucin 1, transmembrane can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology,* Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology,* Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology,* Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology,* Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology,* Volume 2, pp. 11.2.1–11.2.22, John Wiley & Sons, Inc., 1991.

Example 11

Poly (A)+ mRNA isolation

Poly(A)+ mRNA was isolated according to Miura et al., *Clin. Chem.,* 1996, 42, 1758–1764. Other methods for poly(A)+ mRNA isolation are taught in, for example, Ausubel, F. M. et al., *Current Protocols in Molecular Biology,* Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 μL cold PBS. 150 μL Buffer RLT was added to each well and the plate vigorously agitated for 20 seconds. 150 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 μL of Buffer RW1 was added to each well of the RNEASY 96™ M plate and incubated for 15 minutes and the vacuum was again applied for 1 minute. An additional 500 μL of Buffer RW1 was added to each well of the RNEASY 96™ M plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 170 μL water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Mucin 1, Transmembrane mRNA Levels

Quantitation of mucin 1, transmembrane mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM, obtained from either Operon Technologies Inc., Alameda, Calif. or Integrated DNA Technologies Inc., Coralville, Iowa) is attached to the 5' end of the probe and a quencher dye (e.g., TAMRA, obtained from either Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen, Carlsbad, Calif. RT-PCR reactions were carried out by adding 20 μL PCR cocktail (2.5×PCR buffer (−MgCl2), 6.6 mM MgCl2, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96 well plates containing 30 μL total RNA solution. The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreenTM (Molecular Probes, Inc. Eugene, Oreg.). GAPDH expression is quantified by real time RT-PCR, by being run simultaneously with the target, multiplexing, or separately. Total RNA is quantified using RiboGreenTM RNA quantification reagent from Molecular Probes. Methods of RNA quantification by RiboGreenTM are taught in Jones, L. J., et al, Analytical Biochemistry, 1998, 265, 368–374.

In this assay, 170 μL of RiboGreenTM working reagent (RiboGreenTM reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 480 nm and emission at 520 nm.

Probes and primers to human mucin 1, transmembrane were designed to hybridize to a human mucin 1, transmembrane sequence, using published sequence information (GenBank accession number NM_002456.1, incorporated herein as SEQ ID NO:3). For human mucin 1, transmembrane the PCR primers were: forward primer: TGACTCTG-GCCTTCCGAGAA (SEQ ID NO: 4) reverse primer: GCT-GCTTCCGTTTTATACTGATTG (SEQ ID NO: 5) and the PCR probe was: FAM-TACCATCAATGTCC-ACGACGTGGAGACA-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were: forward primer: GAAGGTGAAGGTCGGAGTC(SEQ ID NO:7) reverse primer: GAAGATGGTGATGGGATTTC (SEQ ID NO:8) and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Mucin 1, Transmembrane mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human mucin 1, transmembrane, a human mucin 1, transmembrane specific probe was prepared by PCR using the forward primer TGACTCTGGCCTTC-CGAGAA (SEQ ID NO: 4) and the reverse primer GCT-GCTTCCGTTTTATACTGATTG (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Mucin 1, Transmembrane Expression by Chimeric Phosphorothioate Oligonucleotides Having 2'-MOE Wings and a Deoxy Gap In accordance with the present invention, a series of oligonucleotides were designed to target different regions of the human mucin 1, transmembrane RNA, using published sequences (GenBank accession number NM_002456.1, representing the main mRNA of mucin 1, transmembrane, incorporated herein as SEQ ID NO: 3; GenBank accession number AF125525.1, representing the variant MUC1/Y, incorporated herein as SEQ ID NO: 10; GenBank accession number AF348143.1, representing a variant of mucin 1, transmembrane herein designated MUC1-II, incorporated herein as SEQ ID NO: 11; GenBank accession number AI834269.1, representing a variant of mucin 1, transmembrane herein designated MUC1-III, the complement of which is incorporated herein as SEQ ID NO: 12; GenBank accession number AW369441.1, representing a variant of mucin 1, transmembrane herein designated MUC1-IV, incorporated herein as SEQ ID NO: 14; GenBank accession number BG774910.1, representing a variant of mucin 1, transmembrane herein designated MUC1-V, incorporated herein as SEQ ID NO: 16; GenBank accession number J05581.1, representing a variant of mucin 1, transmembrane herein designated MUC1-VI, incorporated herein as SEQ ID NO: 17; GenBank accession number M31823.1, representing a variant of mucin 1, transmembrane herein designated MUC1-VII, incorporated herein as SEQ ID NO: 18; GenBank accession number M61170, representing a genomic sequence of mucin 1, transmembrane, incorporated herein as SEQ ID NO: 19; GenBank accession number U60259.1, representing the variant MUC1/X, incorporated herein as SEQ ID NO: 20; and GenBank accession number Z17325.1, representing the variant MUC1/D, incorporated herein as SEQ ID NO: 21). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3'directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human mucin 1, transmembrane mRNA levels by quantative real-time PCR as described in other examples herein. Data are averages from two experiments. If present, "N.D." indicates "no data".

TABLE 1

Inhibition of human mucin 1, transmembrane mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 199396 | 5'UTR | 3 | 8 | gaacagattcaagcagccag | 0 | 22 |
| 199397 | Start Codon | 3 | 49 | cccggtgtcatggtggtggt | 58 | 23 |

TABLE 1-continued

Inhibition of human mucin 1, transmembrane mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 199398 | Start Codon | 3 | 52 | gtgcccggtgtcatggtggt | 58 | 24 |
| 199399 | Coding | 3 | 65 | gaaaggagactgggtgcccg | 54 | 25 |
| 199400 | Coding | 3 | 105 | ctgtaacaactgtaagcact | 41 | 26 |
| 199401 | Coding | 3 | 107 | acctgtaacaactgtaagca | 53 | 27 |
| 199402 | Coding | 3 | 187 | tcagtagagctgggcactga | 55 | 28 |
| 199403 | Coding | 3 | 196 | gcattcttctcagtagagct | 77 | 29 |
| 199404 | Coding | 3 | 197 | agcattcttctcagtagagc | 50 | 30 |
| 199405 | Coding | 3 | 210 | tggtcatactcacagcattc | 42 | 31 |
| 199406 | Coding | 3 | 214 | ctgctggtcatactcacagc | 56 | 32 |
| 199407 | Coding | 3 | 227 | gctggagagtacgctgctgg | 57 | 33 |
| 199408 | Coding | 3 | 344 | tgggaccgaggtgacatcct | 65 | 34 |
| 199409 | Coding | 3 | 694 | gtgacattgtggactggagg | 55 | 35 |
| 199410 | Coding | 3 | 697 | gaggtgacattgtggactgg | 57 | 36 |
| 199411 | Coding | 3 | 704 | tgaggccgaggtgacattgt | 54 | 37 |
| 199412 | Coding | 3 | 829 | gtggtaggagtatcagagtg | 53 | 38 |
| 199413 | Coding | 3 | 835 | gcaagggtggtaggagtatc | 50 | 39 |
| 199414 | Coding | 3 | 860 | ggcatcagtcttggtgctat | 53 | 40 |
| 199415 | Coding | 3 | 940 | gagacccagtagacaactg | 24 | 41 |
| 199416 | Coding | 3 | 997 | tcttccagagaggaattaaa | 41 | 42 |
| 199417 | Coding | 3 | 1037 | aatgtctctctgcagctctt | 41 | 43 |
| 199418 | Coding | 3 | 1042 | tcagaaatgtctctctgcag | 54 | 44 |
| 199419 | Coding | 3 | 1056 | tctgcaaaaacatttcagaa | 45 | 45 |
| 199420 | Coding | 3 | 1065 | gtttataaatctgcaaaaac | 39 | 46 |
| 199421 | Coding | 3 | 1091 | attggagaggcccagaaaac | 41 | 47 |
| 199422 | Coding | 3 | 1095 | taatattggagaggcccaga | 50 | 48 |
| 199423 | Coding | 3 | 1100 | gaacttaatattggagaggc | 48 | 49 |
| 199424 | Coding | 3 | 1112 | agatcctggcctgaacttaa | 53 | 50 |
| 199425 | Coding | 3 | 1115 | cacagatcctggcctgaact | 49 | 51 |
| 199426 | Coding | 3 | 1168 | acgtcgtggacattgatggt | 84 | 52 |
| 199427 | Coding | 3 | 1217 | gttatatcgagaggctgctt | 50 | 53 |
| 199428 | Coding | 3 | 1225 | atcgtcaggttatatcgaga | 47 | 54 |
| 199429 | Coding | 3 | 1251 | gcacatcactcacgctgacg | 50 | 55 |
| 199430 | Coding | 3 | 1268 | ggcagagaaaggaaatggca | 46 | 56 |
| 199431 | Coding | 3 | 1371 | gacagacagccaaggcaatg | 47 | 57 |
| 199432 | Coding | 3 | 1397 | ctgcccgtagttctttcggc | 43 | 58 |
| 199433 | Coding | 3 | 1412 | tggaaagatgtccagctgcc | 41 | 59 |
| 199434 | Coding | 3 | 1499 | gctacgatcggtactgctag | 52 | 60 |
| 199435 | Coding | 3 | 1540 | aggctgctgccaccattacc | 59 | 61 |
| 199436 | Coding | 3 | 1582 | aagttggcagaagtggctgc | 42 | 62 |
| 199437 | Stop Codon | 3 | 1586 | ctacaagttggcagaagtgg | 35 | 63 |
| 199438 | Stop Codon | 3 | 1594 | acgtgcccctacaagttggc | 57 | 64 |
| 199439 | 3'UTR | 3 | 1606 | gctcagagggcgacgtgccc | 36 | 65 |
| 199440 | 3'UTR | 3 | 1617 | ctgccactcagctcagagg | 56 | 66 |
| 199441 | 3'UTR | 3 | 1622 | actggctggccactcagctc | 55 | 67 |
| 199442 | 3'UTR | 3 | 1630 | ggaatggcactggctggcca | 60 | 68 |
| 199443 | 3'UTR | 3 | 1635 | ggagtggaatggcactggct | 56 | 69 |
| 199444 | Coding | 10 | 141 | aggaattaaaagcattcttc | 7 | 70 |
| 199445 | Coding | 11 | 174 | cagtagacaaagcattcttc | 40 | 71 |
| 199446 | Coding | 11 | 297 | gacagacagccatttcagaa | 80 | 72 |
| 199447 | Exon: Exon Junction | 12 | 49 | catcactcactgaacttaat | 1 | 73 |
| 199448 | Intron 6 | 19 | 5327 | tttgggttttccaagtaccc | 83 | 74 |
| 199449 | Intron 6 | 19 | 5436 | catagtctcctcccaggcct | 44 | 75 |
| 199450 | Intron 6 | 19 | 5588 | cattttgcctctgggtgcaa | 49 | 76 |
| 199451 | Exon: Exon Junction | 14 | 160 | cagccccagacatttcagaa | 21 | 77 |
| 199452 | Intron 1 | 19 | 3289 | ttctctctgcccataggcct | 42 | 78 |
| 199453 | Intron 1 | 19 | 3426 | gggtcttttatgaaggaaaa | 43 | 79 |
| 199454 | Exon: Exon Junction | 16 | 455 | acatcactcacatttcagaa | 62 | 80 |
| 199455 | 3'UTR | 17 | 1776 | accacgttttattcagtcca | 65 | 81 |
| 199456 | Coding | 18 | 115 | gctgtggtagctgtaagcac | 38 | 82 |
| 199457 | Coding | 20 | 175 | gtgctgggatagcattcttc | 15 | 83 |
| 199458 | Coding | 20 | 245 | agagtcaattgtaccaccac | 2 | 84 |
| 199459 | Coding | 21 | 122 | ttttctccacctgtaagcac | 18 | 85 |

TABLE 1-continued

Inhibition of human mucin 1, transmembrane mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 199460 | Intron: Exon Junction | 19 | 3489 | cctgtaacaactgttgcggg | 32 | 86 |
| 199461 | Intron: Exon Junction | 19 | 3498 | tgaccagaacctgtaacaac | 38 | 87 |
| 199462 | Exon 2d | 19 | 3530 | tctccttttctccacctggg | 49 | 88 |
| 199463 | Exon 2d | 19 | 3571 | ctcagtagagctgggcactg | 47 | 89 |
| 199464 | Exon 2d | 19 | 3590 | tcatactcacagcattcttc | 42 | 90 |
| 199465 | Exon: Intron Junction | 19 | 3973 | agagcctgaggccgaggtga | 58 | 91 |
| 199466 | Intron: Exon Junction | 19 | 4201 | gaccccagtagacaactggg | 20 | 92 |
| 199467 | Intron: Exon Junction | 19 | 4250 | aggaattaaactggaggttt | 55 | 93 |
| 199468 | Exon 3d | 19 | 4269 | gtgctgggatcttccagaga | 61 | 94 |
| 199469 | Intron: Exon Junction | 19 | 4621 | atcctggcctggtcacaggg | 39 | 95 |
| 199470 | Exon 5 | 19 | 4936 | cagccccagactgggcagag | 41 | 96 |
| 199471 | Intron 6 | 19 | 5449 | ggcccctttcttccatagtc | 55 | 97 |
| 199472 | Intron 6 | 19 | 5889 | ccacctggagtggttttcca | 42 | 98 |
| 199473 | Intron 6 | 19 | 5956 | aaagccgagagagggaggtc | 51 | 99 |

As shown in Table 1, SEQ ID NOs 23, 24, 25, 26, 27, 28, 29, 30, 31, 32, 33, 34, 35, 36, 37, 38, 39, 40, 42, 43, 44, 45, 47, 48, 49, 50, 51, 52, 53, 54, 55, 56, 57, 58, 59, 60, 61, 62, 64, 66, 67, 68, 69, 72, 74, 75, 76, 78, 79, 80, 81, 88, 89, 90, 91, 93, 94, 96, 97, 98 and 99 demonstrated at least 41% inhibition of human mucin 1, transmembrane expression in this assay and are therefore preferred. The target sites to which these preferred sequences are complementary are herein referred to as "active sites" and are therefore preferred sites for targeting by compounds of the present invention.

Example 16

Western Blot Analysis of Mucin 1, Transmembrane Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to mucin 1, transmembrane is used, with a radiolabelled or fluorescently labeled secondary antibody directed against the primary antibody species. Bands are visualized using a PHOSPHO-RIMAGER™ (Molecular Dynamics, Sunnyvale Calif.).

Example 17

Targeting of Individual Oligonucleotides to Specific Variants of Mucin 1, Transmembrane It is advantageous to selectively inhibit the expression of one or more variants of mucin 1, transmembrane. Consequently, in one embodiment of the present invention are oligonucleotides that selectively target, hybridize to, and specifically inhibit one or more, but fewer than all of the variants of mucin 1, transmembrane. A summary of the target sites of the variants is shown in Table 2 and includes Genbank accession number NM_002456.1, representing mucin 1, transmembrane (MUC1), incorporated herein as SEQ ID NO: 3; Genbank accession number AF125525.1, representing MUC1/Y, incorporated herein as SEQ ID NO: 10; Genbank accession number AF348143.1, representing MUC1-II, incorporated herein as SEQ ID NO: 11; Genbank accession number AI834269.1, representing MUC1-III, incorporated herein as SEQ ID NO: 12; Genbank accession number AW369441.1, representing MUC1-IV, incorporated herein as SEQ ID NO: 14; Genbank accession number BG774910.1, representing MUC1-V, incorporated herein as SEQ ID NO: 16; Genbank accession number J05581.1, representing MUC1-VI, incorporated herein as SEQ ID NO: 17; Genbank accession number M31823.1, representing MUC1-VII, incorporated herein as SEQ ID NO: 18; Genbank accession number U60259.1, representing MUC1/X, incorporated herein as SEQ ID NO: 20; Genbank accession number Z17325.1, representing MUC1/D, incorporated herein as SEQ ID NO: 21; Genbank accession number S81781.1, representing the variant MUC1/A, incorporated herein as SEQ ID NO: 100; Genbank accession number M32738.1, representing the variant MUC1/REP, incorporated herein as SEQ ID NO: 101; Genbank accession number M35093.1, representing the variant MUC1/SEC, incorporated herein as SEQ ID NO: 102; Genbank accession number U60261.1, representing the variant MUC1/Z, incorporated herein as SEQ ID NO: 103; Genbank accession number Z17324.1, representing the variant MUC1/C, incorporated herein as SEQ ID NO: 104; Genbank accession number BF876382.1, representing a variant of mucin 1, transmembrane herein designated MUC1-VIII, incorporated herein as SEQ ID NO: 105; Genbank accession number BG541121.1, representing a variant of mucin 1, transmembrane herein designated MUC1-IX, incorporated herein as SEQ ID NO: 106; Genbank accession number AL046435.1, representing a variant of mucin 1, transmembrane herein designated MUC1-X, incorporated herein as SEQ ID NO: 107.

TABLE 2

Targeting of individual oligonucleotides to specific variants of mucin 1, transmembrane

| ISIS # | OLIGO SEQ ID NO. | TARGET SITE | VARIANT | VARIANT SEQ ID NO. |
|---|---|---|---|---|
| 199396 | 22 | 8 | MUC1 | 3 |
| 199397 | 23 | 49 | MUC1 | 3 |
| 199397 | 23 | 16 | MUC1-II | 11 |
| 199397 | 23 | 64 | MUC1-VI | 17 |
| 199397 | 23 | 58 | MUC1-VII | 18 |
| 199397 | 23 | 17 | MUC1/X | 20 |
| 199397 | 23 | 65 | MUC1/D | 21 |
| 199397 | 23 | 1 | MUC1/A | 100 |
| 199397 | 23 | 42 | MUC1/REP | 101 |
| 199397 | 23 | 776 | MUC1/SEC | 102 |
| 199397 | 23 | 17 | MUC1/Z | 103 |
| 199397 | 23 | 65 | MUC1/C | 104 |
| 199397 | 23 | 59 | MUC1-IX | 106 |
| 199398 | 24 | 52 | MUC1 | 3 |
| 199398 | 24 | 19 | MUC1-II | 11 |
| 199398 | 24 | 67 | MUC1-VI | 17 |
| 199398 | 24 | 61 | MUC1-VII | 18 |
| 199398 | 24 | 20 | MUC1/X | 20 |
| 199398 | 24 | 68 | MUC1/D | 21 |
| 199398 | 24 | 4 | MUC1/A | 100 |
| 199398 | 24 | 45 | MUC1/REP | 101 |
| 199398 | 24 | 779 | MUC1/SEC | 102 |
| 199398 | 24 | 20 | MUC1/Z | 103 |
| 199398 | 24 | 68 | MUC1/C | 104 |
| 199398 | 24 | 62 | MUC1-IX | 106 |
| 199399 | 25 | 65 | MUC1 | 3 |
| 199399 | 25 | 8 | MUC1/Y | 10 |
| 199399 | 25 | 32 | MUC1-II | 11 |
| 199399 | 25 | 80 | MUC1-VI | 17 |
| 199399 | 25 | 74 | MUC1-VII | 18 |
| 199399 | 25 | 33 | MUC1/X | 20 |
| 199399 | 25 | 81 | MUC1/D | 21 |
| 199399 | 25 | 17 | MUC1/A | 100 |
| 199399 | 25 | 58 | MUC1/REP | 101 |
| 199399 | 25 | 792 | MUC1/SEC | 102 |
| 199399 | 25 | 33 | MUC1/Z | 103 |
| 199399 | 25 | 81 | MUC1/C | 104 |
| 199399 | 25 | 75 | MUC1-IX | 106 |
| 199400 | 26 | 105 | MUC1 | 3 |
| 199400 | 26 | 72 | MUC1-II | 11 |
| 199400 | 26 | 120 | MUC1-VI | 17 |
| 199400 | 26 | 73 | MUC1/X | 20 |
| 199400 | 26 | 73 | MUC1/Z | 103 |
| 199401 | 27 | 107 | MUC1 | 3 |
| 199401 | 27 | 74 | MUC1-II | 11 |
| 199401 | 27 | 122 | MUC1-VI | 17 |
| 199401 | 27 | 75 | MUC1/X | 20 |
| 199401 | 27 | 75 | MUC1/Z | 103 |
| 199402 | 28 | 187 | MUC1 | 3 |
| 199402 | 28 | 121 | MUC1/Y | 10 |
| 199402 | 28 | 154 | MUC1-II | 11 |
| 199402 | 28 | 202 | MUC1-VI | 17 |
| 199402 | 28 | 223 | MUC1-VII | 18 |
| 199402 | 28 | 155 | MUC1/X | 20 |
| 199402 | 28 | 166 | MUC1/A | 100 |
| 199402 | 28 | 207 | MUC1/REP | 101 |
| 199402 | 28 | 1413 | MUC1/SEC | 102 |
| 199402 | 28 | 155 | MUC1/Z | 103 |
| 199402 | 28 | 346 | MUC1-VIII | 105 |
| 199402 | 28 | 224 | MUC1-IX | 106 |
| 199403 | 29 | 196 | MUC1 | 3 |
| 199403 | 29 | 130 | MUC1/Y | 10 |
| 199403 | 29 | 163 | MUC1-II | 11 |
| 199403 | 29 | 211 | MUC1-VI | 17 |
| 199403 | 29 | 232 | MUC1-VII | 18 |
| 199403 | 29 | 164 | MUC1/X | 20 |
| 199403 | 29 | 175 | MUC1/A | 100 |
| 199403 | 29 | 216 | MUC1/REP | 101 |
| 199403 | 29 | 1422 | MUC1/SEC | 102 |
| 199403 | 29 | 164 | MUC1/Z | 103 |
| 199403 | 29 | 355 | MUC1-VIII | 105 |
| 199403 | 29 | 233 | MUC1-IX | 106 |
| 199404 | 30 | 197 | MUC1 | 3 |
| 199404 | 30 | 131 | MUC1/Y | 10 |
| 199404 | 30 | 164 | MUC1-II | 11 |
| 199404 | 30 | 212 | MUC1-VI | 17 |
| 199404 | 30 | 233 | MUC1-VII | 18 |
| 199404 | 30 | 165 | MUC1/X | 20 |
| 199404 | 30 | 176 | MUC1/A | 100 |
| 199404 | 30 | 217 | MUC1/REP | 101 |
| 199404 | 30 | 1423 | MUC1/SEC | 102 |
| 199404 | 30 | 165 | MUC1/Z | 103 |
| 199404 | 30 | 356 | MUC1-VIII | 105 |
| 199404 | 30 | 234 | MUC1-IX | 106 |
| 199405 | 31 | 210 | MUC1 | 3 |
| 199405 | 31 | 225 | MUC1-VI | 17 |
| 199405 | 31 | 246 | MUC1-VII | 18 |
| 199405 | 31 | 189 | MUC1/A | 100 |
| 199405 | 31 | 230 | MUC1/REP | 101 |
| 199405 | 31 | 1436 | MUC1/SEC | 102 |
| 199405 | 31 | 369 | MUC1-VIII | 105 |
| 199406 | 32 | 214 | MUC1 | 3 |
| 199406 | 32 | 229 | MUC1-VI | 17 |
| 199406 | 32 | 250 | MUC1-VII | 18 |
| 199406 | 32 | 193 | MUC1/A | 100 |
| 199406 | 32 | 234 | MUC1/REP | 101 |
| 199406 | 32 | 1440 | MUC1/SEC | 102 |
| 199406 | 32 | 373 | MUC1-VIII | 105 |
| 199407 | 33 | 227 | MUC1 | 3 |
| 199407 | 33 | 242 | MUC1-VI | 17 |
| 199407 | 33 | 263 | MUC1-VII | 18 |
| 199407 | 33 | 206 | MUC1/A | 100 |
| 199407 | 33 | 247 | MUC1/REP | 101 |
| 199407 | 33 | 1453 | MUC1/SEC | 102 |
| 199407 | 33 | 386 | MUC1-VIII | 105 |
| 199408 | 34 | 344 | MUC1 | 3 |
| 199408 | 34 | 359 | MUC1-VI | 17 |
| 199408 | 34 | 380 | MUC1-VII | 18 |
| 199408 | 34 | 364 | MUC1/REP | 101 |
| 199408 | 34 | 1570 | MUC1/SEC | 102 |
| 199409 | 35 | 694 | MUC1 | 3 |
| 199409 | 35 | 93 | MUC1-V | 16 |
| 199409 | 35 | 589 | MUC1-VI | 17 |
| 199409 | 35 | 1800 | MUC1/SEC | 102 |
| 199410 | 36 | 697 | MUC1 | 3 |
| 199410 | 36 | 96 | MUC1-V | 16 |
| 199410 | 36 | 592 | MUC1-VI | 17 |
| 199410 | 36 | 1803 | MUC1/SEC | 102 |
| 199411 | 37 | 704 | MUC1 | 3 |
| 199411 | 37 | 103 | MUC1-V | 16 |
| 199411 | 37 | 599 | MUC1-VI | 17 |
| 199411 | 37 | 1810 | MUC1/SEC | 102 |
| 199412 | 38 | 829 | MUC1 | 3 |
| 199412 | 38 | 228 | MUC1-V | 16 |
| 199412 | 38 | 724 | MUC1-VI | 17 |
| 199412 | 38 | 1935 | MUC1/SEC | 102 |
| 199413 | 39 | 835 | MUC1 | 3 |
| 199413 | 39 | 234 | MUC1-V | 16 |
| 199413 | 39 | 730 | MUC1-VI | 17 |
| 199413 | 39 | 1941 | MUC1/SEC | 102 |
| 199414 | 40 | 860 | MUC1 | 3 |
| 199414 | 40 | 259 | MUC1-V | 16 |
| 199414 | 40 | 755 | MUC1-VI | 17 |
| 199414 | 40 | 1966 | MUC1/SEC | 102 |
| 199415 | 41 | 940 | MUC1 | 3 |
| 199415 | 41 | 44 | MUC1-IV | 14 |

TABLE 2-continued

Targeting of individual oligonucleotides to specific variants of mucin 1, transmembrane

| ISIS # | OLIGO SEQ ID NO. | TARGET SITE | VARIANT | VARIANT SEQ ID NO. |
|---|---|---|---|---|
| 199415 | 41 | 339 | MUC1-V | 16 |
| 199415 | 41 | 835 | MUC1-VI | 17 |
| 199415 | 41 | 2046 | MUC1/SEC | 102 |
| 199416 | 42 | 997 | MUC1 | 3 |
| 199416 | 42 | 151 | MUC1/Y | 10 |
| 199416 | 42 | 238 | MUC1-II | 11 |
| 199416 | 42 | 101 | MUC1-IV | 14 |
| 199416 | 42 | 396 | MUC1-V | 16 |
| 199416 | 42 | 892 | MUC1-VI | 17 |
| 199416 | 42 | 2103 | MUC1/SEC | 102 |
| 199416 | 42 | 239 | MUC1/Z | 103 |
| 199416 | 42 | 254 | MUC1-IX | 106 |
| 199417 | 43 | 1037 | MUC1 | 3 |
| 199417 | 43 | 191 | MUC1/Y | 10 |
| 199417 | 43 | 278 | MUC1-II | 11 |
| 199417 | 43 | 141 | MUC1-IV | 14 |
| 199417 | 43 | 436 | MUC1-V | 16 |
| 199417 | 43 | 932 | MUC1-VI | 17 |
| 199417 | 43 | 206 | MUC1/X | 20 |
| 199417 | 43 | 2143 | MUC1/SEC | 102 |
| 199417 | 43 | 279 | MUC1/Z | 103 |
| 199417 | 43 | 294 | MUC1-IX | 106 |
| 199418 | 44 | 1042 | MUC1 | 3 |
| 199418 | 44 | 196 | MUC1/Y | 10 |
| 199418 | 44 | 283 | MUC1-II | 11 |
| 199418 | 44 | 146 | MUC1-IV | 14 |
| 199418 | 44 | 441 | MUC1-V | 16 |
| 199418 | 44 | 937 | MUC1-VI | 17 |
| 199418 | 44 | 211 | MUC1/X | 20 |
| 199418 | 44 | 2148 | MUC1/SEC | 102 |
| 199418 | 44 | 284 | MUC1/Z | 103 |
| 199418 | 44 | 299 | MUC1-IX | 106 |
| 199419 | 45 | 1056 | MUC1 | 3 |
| 199419 | 45 | 210 | MUC1/Y | 10 |
| 199419 | 45 | 951 | MUC1-VI | 17 |
| 199419 | 45 | 298 | MUC1/Z | 103 |
| 199419 | 45 | 313 | MUC1-IX | 106 |
| 199420 | 46 | 1065 | MUC1 | 3 |
| 199420 | 46 | 219 | MUC1/Y | 10 |
| 199420 | 46 | 3 | MUC1-III | 12 |
| 199420 | 46 | 960 | MUC1-VI | 17 |
| 199420 | 46 | 2270 | MUC1/SEC | 102 |
| 199420 | 46 | 307 | MUC1/Z | 103 |
| 199420 | 46 | 322 | MUC1-IX | 106 |
| 199421 | 47 | 1091 | MUC1 | 3 |
| 199421 | 47 | 245 | MUC1/Y | 10 |
| 199421 | 47 | 29 | MUC1-III | 12 |
| 199421 | 47 | 986 | MUC1-VI | 17 |
| 199421 | 47 | 2296 | MUC1/SEC | 102 |
| 199421 | 47 | 333 | MUC1/Z | 103 |
| 199421 | 47 | 348 | MUC1-IX | 106 |
| 199422 | 48 | 1095 | MUC1 | 3 |
| 199422 | 48 | 249 | MUC1/Y | 10 |
| 199422 | 48 | 33 | MUC1-III | 12 |
| 199422 | 48 | 990 | MUC1-VI | 17 |
| 199422 | 48 | 2300 | MUC1/SEC | 102 |
| 199422 | 48 | 337 | MUC1/Z | 103 |
| 199422 | 48 | 352 | MUC1-IX | 106 |
| 199423 | 49 | 1100 | MUC1 | 3 |
| 199423 | 49 | 254 | MUC1/Y | 10 |
| 199423 | 49 | 38 | MUC1-III | 12 |
| 199423 | 49 | 995 | MUC1-VI | 17 |
| 199423 | 49 | 2305 | MUC1/SEC | 102 |
| 199423 | 49 | 342 | MUC1/Z | 103 |
| 199423 | 49 | 357 | MUC1-IX | 106 |
| 199424 | 50 | 1112 | MUC1 | 3 |
| 199424 | 50 | 266 | MUC1/Y | 10 |
| 199424 | 50 | 1007 | MUC1-VI | 17 |
| 199424 | 50 | 354 | MUC1/Z | 103 |
| 199424 | 50 | 369 | MUC1-IX | 106 |
| 199425 | 51 | 1115 | MUC1 | 3 |
| 199425 | 51 | 269 | MUC1/Y | 10 |
| 199425 | 51 | 1010 | MUC1-VI | 17 |
| 199425 | 51 | 357 | MUC1/Z | 103 |
| 199425 | 51 | 372 | MUC1-IX | 106 |
| 199426 | 52 | 1168 | MUC1 | 3 |
| 199426 | 52 | 1063 | MUC1-VI | 17 |
| 199426 | 52 | 281 | MUC1/X | 20 |
| 199426 | 52 | 2524 | MUC1/SEC | 102 |
| 199426 | 52 | 410 | MUC1/Z | 103 |
| 199426 | 52 | 425 | MUC1-IX | 106 |
| 199427 | 53 | 1217 | MUC1 | 3 |
| 199427 | 53 | 371 | MUC1/Y | 10 |
| 199427 | 53 | 1112 | MUC1-VI | 17 |
| 199427 | 53 | 330 | MUC1/X | 20 |
| 199427 | 53 | 2573 | MUC1/SEC | 102 |
| 199427 | 53 | 459 | MUC1/Z | 103 |
| 199427 | 53 | 473 | MUC1-IX | 106 |
| 199428 | 54 | 1225 | MUC1 | 3 |
| 199428 | 54 | 379 | MUC1/Y | 10 |
| 199428 | 54 | 1120 | MUC1-VI | 17 |
| 199428 | 54 | 338 | MUC1/X | 20 |
| 199428 | 54 | 2581 | MUC1/SEC | 102 |
| 199428 | 54 | 467 | MUC1/Z | 103 |
| 199428 | 54 | 481 | MUC1-IX | 106 |
| 199429 | 55 | 1251 | MUC1 | 3 |
| 199429 | 55 | 405 | MUC1/Y | 10 |
| 199429 | 55 | 1146 | MUC1-VI | 17 |
| 199429 | 55 | 364 | MUC1/X | 20 |
| 199429 | 55 | 493 | MUC1/Z | 103 |
| 199429 | 55 | 507 | MUC1-IX | 106 |
| 199430 | 56 | 1268 | MUC1 | 3 |
| 199430 | 56 | 422 | MUC1/Y | 10 |
| 199430 | 56 | 69 | MUC1-III | 12 |
| 199430 | 56 | 474 | MUC1-V | 16 |
| 199430 | 56 | 1163 | MUC1-VI | 17 |
| 199430 | 56 | 381 | MUC1/X | 20 |
| 199430 | 56 | 510 | MUC1/Z | 103 |
| 199431 | 57 | 1371 | MUC1 | 3 |
| 199431 | 57 | 525 | MUC1/Y | 10 |
| 199431 | 57 | 250 | MUC1-IV | 14 |
| 199431 | 57 | 577 | MUC1-V | 16 |
| 199431 | 57 | 1266 | MUC1-VI | 17 |
| 199431 | 57 | 484 | MUC1/X | 20 |
| 199431 | 57 | 613 | MUC1/Z | 103 |
| 199431 | 57 | 76 | MUC1-X | 107 |
| 199432 | 58 | 1397 | MUC1 | 3 |
| 199432 | 58 | 551 | MUC1/Y | 10 |
| 199432 | 58 | 276 | MUC1-IV | 14 |
| 199432 | 58 | 603 | MUC1-V | 16 |
| 199432 | 58 | 1292 | MUC1-VI | 17 |
| 199432 | 58 | 510 | MUC1/X | 20 |
| 199432 | 58 | 2977 | MUC1/SEC | 102 |
| 199432 | 58 | 639 | MUC1/Z | 103 |
| 199432 | 58 | 102 | MUC1-X | 107 |
| 199433 | 59 | 1412 | MUC1 | 3 |
| 199433 | 59 | 566 | MUC1/Y | 10 |
| 199433 | 59 | 291 | MUC1-IV | 14 |
| 199433 | 59 | 618 | MUC1-V | 16 |
| 199433 | 59 | 1307 | MUC1-VI | 17 |
| 199433 | 59 | 525 | MUC1/X | 20 |
| 199433 | 59 | 2992 | MUC1/SEC | 102 |
| 199433 | 59 | 654 | MUC1/Z | 103 |
| 199433 | 59 | 117 | MUC1-X | 107 |
| 199434 | 60 | 1499 | MUC1 | 3 |
| 199434 | 60 | 653 | MUC1/Y | 10 |
| 199434 | 60 | 425 | MUC1-II | 11 |
| 199434 | 60 | 378 | MUC1-IV | 14 |
| 199434 | 60 | 704 | MUC1-V | 16 |
| 199434 | 60 | 1394 | MUC1-VI | 17 |
| 199434 | 60 | 612 | MUC1/X | 20 |
| 199434 | 60 | 3078 | MUC1/SEC | 102 |
| 199434 | 60 | 741 | MUC1/Z | 103 |
| 199434 | 60 | 204 | MUC1-X | 107 |
| 199435 | 61 | 1540 | MUC1 | 3 |
| 199435 | 61 | 694 | MUC1/Y | 10 |

TABLE 2-continued

Targeting of individual oligonucleotides to specific variants of mucin 1, transmembrane

| ISIS # | OLIGO SEQ ID NO. | TARGET SITE | VARIANT | VARIANT SEQ ID NO. |
|---|---|---|---|---|
| 199435 | 61 | 466 | MUC1-II | 11 |
| 199435 | 61 | 419 | MUC1-IV | 14 |
| 199435 | 61 | 1435 | MUC1-VI | 17 |
| 199435 | 61 | 653 | MUC1/X | 20 |
| 199435 | 61 | 782 | MUC1/Z | 103 |
| 199436 | 62 | 1582 | MUC1 | 3 |
| 199436 | 62 | 736 | MUC1/Y | 10 |
| 199436 | 62 | 508 | MUC1-II | 11 |
| 199436 | 62 | 786 | MUC1-V | 16 |
| 199436 | 62 | 1477 | MUC1-VI | 17 |
| 199436 | 62 | 695 | MUC1/X | 20 |
| 199436 | 62 | 824 | MUC1/Z | 103 |
| 199437 | 63 | 1586 | MUC1 | 3 |
| 199437 | 63 | 740 | MUC1/Y | 10 |
| 199437 | 63 | 512 | MUC1-II | 11 |
| 199437 | 63 | 790 | MUC1-V | 16 |
| 199437 | 63 | 1481 | MUC1-VI | 17 |
| 199437 | 63 | 699 | MUC1/X | 20 |
| 199437 | 63 | 828 | MUC1/Z | 103 |
| 199438 | 64 | 1594 | MUC1 | 3 |
| 199438 | 64 | 520 | MUC1-II | 11 |
| 199438 | 64 | 798 | MUC1-V | 16 |
| 199438 | 64 | 1489 | MUC1-VI | 17 |
| 199438 | 64 | 707 | MUC1/X | 20 |
| 199438 | 64 | 836 | MUC1/Z | 103 |
| 199439 | 65 | 1606 | MUC1 | 3 |
| 199440 | 66 | 1617 | MUC1 | 3 |
| 199441 | 67 | 1622 | MUC1 | 3 |
| 199441 | 67 | 1517 | MUC1-VI | 17 |
| 199442 | 68 | 1630 | MUC1 | 3 |
| 199442 | 68 | 833 | MUC1-V | 16 |
| 199442 | 68 | 1525 | MUC1-VI | 17 |
| 199443 | 69 | 1635 | MUC1 | 3 |
| 199443 | 69 | 514 | MUC1-IV | 14 |
| 199443 | 69 | 1530 | MUC1-VI | 17 |
| 199444 | 70 | 141 | MUC1/Y | 10 |
| 199444 | 70 | 244 | MUC1-IX | 106 |
| 199445 | 71 | 174 | MUC1-II | 11 |
| 199445 | 71 | 175 | MUC1/Z | 103 |
| 199446 | 72 | 297 | MUC1-II | 11 |
| 199447 | 73 | 49 | MUC1-III | 12 |
| 199448 | 74 | 3171 | MUC1/SEC | 102 |
| 199448 | 74 | 298 | MUC1-X | 107 |
| 199449 | 75 | 3279 | MUC1/SEC | 102 |
| 199449 | 75 | 407 | MUC1-X | 107 |
| 199450 | 76 | 559 | MUC1-X | 107 |
| 199451 | 77 | 160 | MUC1-IV | 14 |
| 199452 | 78 | 1134 | MUC1/SEC | 102 |
| 199452 | 78 | 65 | MUC1-VIII | 105 |
| 199453 | 79 | 1269 | MUC1/SEC | 102 |
| 199453 | 79 | 202 | MUC1-VIII | 105 |
| 199454 | 80 | 455 | MUC1-V | 16 |
| 199455 | 81 | 1776 | MUC1-VI | 17 |
| 199456 | 82 | 115 | MUC1-VII | 18 |
| 199456 | 82 | 58 | MUC1/A | 100 |
| 199456 | 82 | 99 | MUC1/REP | 101 |
| 199456 | 82 | 116 | MUC1-IX | 106 |
| 199457 | 83 | 175 | MUC1/X | 20 |
| 199458 | 84 | 1132 | MUC1 | 3 |
| 199458 | 84 | 286 | MUC1/Y | 10 |
| 199458 | 84 | 1027 | MUC1-VI | 17 |
| 199458 | 84 | 245 | MUC1/X | 20 |
| 199458 | 84 | 2488 | MUC1/SEC | 102 |
| 199458 | 84 | 374 | MUC1/Z | 103 |
| 199458 | 84 | 389 | MUC1-IX | 106 |
| 199459 | 85 | 122 | MUC1/D | 21 |
| 199460 | 86 | 85 | MUC1/A | 100 |
| 199460 | 86 | 126 | MUC1/REP | 101 |
| 199460 | 86 | 1332 | MUC1/SEC | 102 |
| 199461 | 87 | 115 | MUC1 | 3 |
| 199461 | 87 | 82 | MUC1-II | 11 |
| 199461 | 87 | 130 | MUC1-VI | 17 |
| 199461 | 87 | 83 | MUC1/X | 20 |
| 199461 | 87 | 94 | MUC1/A | 100 |
| 199461 | 87 | 135 | MUC1/REP | 101 |
| 199461 | 87 | 1341 | MUC1/SEC | 102 |
| 199461 | 87 | 83 | MUC1/Z | 103 |
| 199462 | 88 | 147 | MUC1 | 3 |
| 199462 | 88 | 81 | MUC1/Y | 10 |
| 199462 | 88 | 114 | MUC1-II | 11 |
| 199462 | 88 | 162 | MUC1-VI | 17 |
| 199462 | 88 | 183 | MUC1-VII | 18 |
| 199462 | 88 | 115 | MUC1/X | 20 |
| 199462 | 88 | 126 | MUC1/A | 100 |
| 199462 | 88 | 167 | MUC1/REP | 101 |
| 199462 | 88 | 1373 | MUC1/SEC | 102 |
| 199462 | 88 | 115 | MUC1/Z | 103 |
| 199462 | 88 | 154 | MUC1/C | 104 |
| 199462 | 88 | 306 | MUC1-VIII | 105 |
| 199462 | 88 | 184 | MUC1-IX | 106 |
| 199463 | 89 | 188 | MUC1 | 3 |
| 199463 | 89 | 122 | MUC1/Y | 10 |
| 199463 | 89 | 155 | MUC1-II | 11 |
| 199463 | 89 | 203 | MUC1-VI | 17 |
| 199463 | 89 | 224 | MUC1-VII | 18 |
| 199463 | 89 | 156 | MUC1/X | 20 |
| 199463 | 89 | 167 | MUC1/A | 100 |
| 199463 | 89 | 208 | MUC1/REP | 101 |
| 199463 | 89 | 1414 | MUC1/SEC | 102 |
| 199463 | 89 | 156 | MUC1/Z | 103 |
| 199463 | 89 | 347 | MUC1-VIII | 105 |
| 199463 | 89 | 225 | MUC1-IX | 106 |
| 199464 | 90 | 207 | MUC1 | 3 |
| 199464 | 90 | 222 | MUC1-VI | 17 |
| 199464 | 90 | 243 | MUC1-VII | 18 |
| 199464 | 90 | 186 | MUC1/A | 100 |
| 199464 | 90 | 227 | MUC1/REP | 101 |
| 199464 | 90 | 1433 | MUC1/SEC | 102 |
| 199464 | 90 | 366 | MUC1-VIII | 105 |
| 199465 | 91 | 710 | MUC1 | 3 |
| 199465 | 91 | 109 | MUC1-V | 16 |
| 199465 | 91 | 605 | MUC1-VI | 17 |
| 199465 | 91 | 1816 | MUC1/SEC | 102 |
| 199466 | 92 | 938 | MUC1 | 3 |
| 199466 | 92 | 42 | MUC1-IV | 14 |
| 199466 | 92 | 337 | MUC1-V | 16 |
| 199466 | 92 | 833 | MUC1-VI | 17 |
| 199466 | 92 | 2044 | MUC1/SEC | 102 |
| 199467 | 93 | 987 | MUC1 | 3 |
| 199467 | 93 | 228 | MUC1-II | 11 |
| 199467 | 93 | 91 | MUC1-IV | 14 |
| 199467 | 93 | 386 | MUC1-V | 16 |
| 199467 | 93 | 882 | MUC1-VI | 17 |
| 199467 | 93 | 2093 | MUC1/SEC | 102 |
| 199467 | 93 | 229 | MUC1/Z | 103 |
| 199468 | 94 | 1006 | MUC1 | 3 |
| 199468 | 94 | 160 | MUC1/Y | 10 |
| 199468 | 94 | 247 | MUC1-II | 11 |
| 199468 | 94 | 110 | MUC1-IV | 14 |
| 199468 | 94 | 405 | MUC1-V | 16 |
| 199468 | 94 | 901 | MUC1-VI | 17 |
| 199468 | 94 | 2112 | MUC1/SEC | 102 |
| 199468 | 94 | 248 | MUC1/Z | 103 |
| 199468 | 94 | 263 | MUC1-IX | 106 |
| 199469 | 95 | 2466 | MUC1/SEC | 102 |
| 199470 | 96 | 1281 | MUC1 | 3 |
| 199470 | 96 | 435 | MUC1/Y | 10 |
| 199470 | 96 | 82 | MUC1-III | 12 |
| 199470 | 96 | 487 | MUC1-V | 16 |
| 199470 | 96 | 1176 | MUC1-VI | 17 |
| 199470 | 96 | 394 | MUC1/X | 20 |
| 199470 | 96 | 523 | MUC1/Z | 103 |
| 199470 | 96 | 538 | MUC1-IX | 106 |
| 199471 | 97 | 3292 | MUC1/SEC | 102 |
| 199471 | 97 | 420 | MUC1-X | 107 |

What is claimed is:

1. A compound 8 to 50 nucleobases in length targeted to nucleobases 187 through 246, nucleobases 344 through 363, nucleobases 694 through 723, nucleobases 829 through 854, nucleobases 860 through 879, nucleobases 940 through 959, nucleobases 997 through 1016, nucleobases 1037 through 1084, nucleobases 1091 through 1134, nucleobases 1168 through 1187, nucleobases 1251 through 1287, nucleobases 1371 through 1390, nucleobases 1397 through 1431, nucleobases 1499 through 1518, nucleobases 1540 through 1559, or nucleobases 1582 through 1601 of a coding region, nucleobases 1586 through 1613 of a stop codon region, or nucleobases 1606 through 1654 of a 3'-untranslated region of a nucleic acid molecule encoding mucin 1, transmembrane of SEQ ID NO: 3, wherein said compound specifically hybridizes with one of said regions and inhibits the expression of mucin 1, transmembrane.

2. The compound of claim 1 which is an antisense oligonucleotide.

3. The compound of claim 2 wherein the antisense oligonucleotide comprises at least one modified internucleoside linkage.

4. The compound of claim 3 wherein the modified internucleoside linkage is a phosphorothioate linkage.

5. The compound of claim 2 wherein the antisense oligonucleotide comprises at least one modified sugar moiety.

6. The compound of claim 5 wherein the modified sugar moiety is a 2'-O-methoxyethyl sugar moiety.

7. The compound of claim 2 wherein the antisense oligonucleotide comprises at least one modified nucleobase.

8. The compound of claim 7 wherein the modified nucleobase is a 5-methylcytosine.

9. The compound of claim 2 wherein the antisense oligonucleotide is a chimeric oligonucleotide.

10. A composition comprising the compound of claim 1 and a pharmaceutically acceptable carrier or diluent.

11. The composition of claim 10 further comprising a colloidal dispersion system.

12. The composition of claim 10 wherein the compound is an antisense oligonucleotide.

13. A method of inhibiting the expression of mucin 1, transmembrane in cells or tissues comprising contacting said cells or tissues in vitro with the compound of claim 1 so that expression of mucin 1, transmembrane is inhibited.

* * * * *